(12) United States Patent
Chait et al.

(10) Patent No.: US 7,341,874 B2
(45) Date of Patent: *Mar. 11, 2008

(54) METHOD FOR DETECTING POST-TRANSLATION MODIFICATIONS OF PEPTIDES

(75) Inventors: Brian T. Chait, New York, NY (US); Ronald Beavis, Winnipeg (CA); Rong Wang, New York, NY (US); Stephen B. H. Kent, San Francisco, CA (US)

(73) Assignees: The Rockefeller University, New York, NY (US); The Scripps Research Institute, La Jolla, CA (US)

( * ) Notice: Subject to any disclaimer, the term of this patent is extended or adjusted under 35 U.S.C. 154(b) by 329 days.

This patent is subject to a terminal disclaimer.

(21) Appl. No.: 10/792,176

(22) Filed: Mar. 2, 2004

(65) Prior Publication Data

US 2004/0265944 A1 Dec. 30, 2004

Related U.S. Application Data

(63) Continuation of application No. 09/828,326, filed on Apr. 5, 2001, now Pat. No. 6,750,061, which is a continuation of application No. 08/341,555, filed on Jun. 24, 1996, now Pat. No. 6,271,037, which is a continuation-in-part of application No. 07/891,177, filed on May 29, 1992, now abandoned.

(51) Int. Cl.
*G01N 33/00* (2006.01)
(52) U.S. Cl. .................. 436/89; 436/173; 436/174; 436/178; 530/333; 530/402; 250/281; 250/282
(58) Field of Classification Search ................. 436/89, 436/173, 174, 178; 250/281, 282
See application file for complete search history.

(56) References Cited

U.S. PATENT DOCUMENTS

| | | | |
|---|---|---|---|
| 5,008,372 A * | 4/1991 | Wellner | 530/345 |
| 5,045,694 A | 9/1991 | Beavis et al. | |
| 5,118,937 A | 6/1992 | Hillenkamp et al. | |
| 5,144,006 A * | 9/1992 | Tam | 530/345 |
| 5,281,538 A | 1/1994 | Cottrell et al. | |
| 5,288,644 A | 2/1994 | Beavis et al. | |
| 5,328,840 A * | 7/1994 | Coller | 435/7.25 |
| 5,432,260 A * | 7/1995 | Stahl | 530/322 |
| 6,271,037 B1 * | 8/2001 | Chait et al. | 436/89 |
| 6,750,061 B2 * | 6/2004 | Chait et al. | 436/89 |

FOREIGN PATENT DOCUMENTS

| EP | 529 604 A1 | 3/1993 |
|---|---|---|
| WO | WO 94/06017 | 3/1994 |

OTHER PUBLICATIONS

Chait BT, Wang R, Beavis RC, Kent SBH, Protein Ladder Sequencing, Science, 1993, 262: 89-92.*
Hunt DF, Buko AM, Ballard JM, Shabanowitz J, Giordani AB, Sequence Analysis of Polypeptide by Collision Activated Dissociation on a Triple Quadrupole Mass Spectrometer, Biomedical Mass Spectrometry, 1981, 8(9): 397-408.*
Qin J, Steenvoorden RJJM, Chait BT, A Practical Ion Trap Mass Spectrometer for the ANalysis of Peptides by Martix-Assisted Laser Desorption/Ionization, Analytical Chemistry, 1996, 68(10): 1784-1791.*
Beavis RC, Chait BT, Rapic, Sensitive Analysis of Protein Mixtures by Mass Spectrometry, Proceedings of the National Academy of Sciences, U.S.A, 1990, 87: 6873-6877.*
Cooks RG, Kaiser RE, Jr., Quadrupole Ion Trap Mass Spectrometry, Acc. Chem. Res., 1990, 23: 213-219.*
Merrifield RB, Solid Phase Synthesis. I. The Synthesis of a Tetrapeptide, Journal of American Chemical Society, 1963, 85(14): 2149-2154.*
Smith, L.A. et al., "Following Enzyme Catalysis in Real-Time Inside a Fast Atom Bombardment Mass Spectrometer" *Biomed. Mass Spectrom* 10:98 (1983).
Tarr, G.E. "Improved Manual Sequencing Methods" *Methods Enzymology* 47:355 (1977).
Kent, S.H. "Chemical Synthesis Of Peptides And Proteins" *Annual Rev. Biochem.* 57:957-984.
Tsugita et al "C-terminal sequencing of protein: A novel partial acid hydrolysis and analysis by mass spectrometry" *Eur. J. Biochem.* 206:691-696.
Chait et al. "A New Approach For Sequencing Peptides and Proteins" *The 40th ASMS Conference*, Jun. 5, 1992 pp. 1939-1940 (1992).
Beavis et al. "α-Cyano-4-hydroxycinnamic Acid as a Matrix for Matrix-assisted Laser Desorption Mass Spectrometry" *Organic Mass Spectrometry* 27:156-158 (1992).
Aebersold et al. "Design, synthesis, and characterization of a protein sequencing reagent yielding amino acid derivatives with enhanced detectability by mass spectrometry" *Protein Science* 1:494-503 (1992).
Schnolzer et al. "In situ neutralization in Boc-chemistry solid phase peptide synthesis" *Int. J. Peptide Protein Res.* 40:180-193 (1992).
Chait et al. "Weighing Naked Proteins: Practical, High-Accuracy Mass Measurement of Peptides and Proteins" *Science* 257:1885-1894. (1992).
Hillenkamp et al. "Matrix-Assisted Laser Desorption/Ionization Mass Spectrometry of Biopolymers" *Anal. Chem.* 63:1193-1202 (1991).
Beavis et al. "High-Accuracy Molecular Mass Determination of Proteins Using Matrix-Assisted Laser Desorption Mass Spectrometry" *Anal. Chem.* 62:1836-1840 (1990).
Beavis et al. "Factors Affecting the Ultraviolet Laser Desorption of Proteins" *Rap. Comm. Mass Spec.* 3:233 (1989).
Beavis et al. "Matrix Assisted UV Laser Desorption Of Biologically Interesting Molecules" *The 37th ASMS Conference*, Miami Beach, FL, pp. 1186-1187 (May 21-26, 1989).

(Continued)

*Primary Examiner*—Anish Gupta
*Assistant Examiner*—Julie Ha
(74) *Attorney, Agent, or Firm*—Townsend and Townsend and Crew LLP

(57) ABSTRACT

This invention provides for novel methods of identifying covalent modifications of an amino acid residue in a polypeptide chain by detecting mass differences.

7 Claims, 16 Drawing Sheets

OTHER PUBLICATIONS

Noren et al, "A General Method for Site-Specific Incorporation of Unnatural Amino Acids into Proteins" *Science* 244:182-188 (1989).

Karas et al "Matrix-Assisted Ultraviolet Laser Desorption of Non-Volatile Compounds" *International Journal Of Mass Spectrometry and Ion Processes*, 78:53-68 (1987).

Chait et al., "Mass Spectrometric Characterization Of Microscale Enzyme Catalyzed Reactions Of Surface-Bound Peptides And Proteins" *Methods In Protein Sequence Analysis* ed K.A. Walsh, *The Humana Press* pp. 483-492 (1986).

Karas et al. "Influence of the Wavelength in High-Irradiance Ultraviolet Laser Desorption Mass Spectrometry of Organic Molecules" *Anal. Chem.*, 57:2935-2939 (1985).

Self, R. et al., "The Combined Use of Enzymatic Hydrolysis and Fast Atom Bombardment Mass Spectrometry for Peptide Sequencing" *Biomedical Mass Spectrometry* 10:78-82 (1983).

Watson, J.D. et al. "Restriction Fragments Lead to Powerful New Methods for Sequencing DNA" *Recombinant DNA—A Short Course*, W.H. Freeman and Co., New York. pp. 61-63 (1983).

Tsugita et al "Exopeptidase Digestion In Combination With Field Desorption Mass Spectrometry For Amino Acid Sequence Determination" *FEBS* 137:19-24 (1982).

Stryer, L. *Biochemistry, 2nd Ed.*, W.H. Freeman and Co., New York, p. 663 (1981).

Schroeder, W. "Degradation of Peptides by the Edman Method with Direct Identification of the Phenylthiohydantoin-Amino Acid" *Methods in Enzymol.* 25:298-313 (1972).

Richards, F. et al., "Mass Spectroscopy of Methylthiohydantoin Amino Acids: Identification, Quantitation, and the Analysis of Mixtures" *Methods in Enzymol.*, 25:314-325 (1972).

Konigsberg, W. "Subtractive Edman Degradation" *Methods in Enzymol.* 25:326-332 (1972).

\* cited by examiner 1-2-3-4-5-6-7-8-9-..................-n-(OH)

INTACT STARTING

PEPTIDE CHAIN (X)-1-2-3-4-5-6-7-8-9..................-n-(OH)

(X)-2-3-4-5-6-7-8-9-..................-n-(OH)

(X)-3-4-5-6-7-8-9..................-n-(OH)

(X)-4-5-6-7-8-9..................-n-(OH)

(X)-5-6-7-8-9..................-n-(OH)

etc.

FIG.1

METHOD FOR DETECTING POST-TRANSLATION MODIFICATIONS OF PEPTIDES

RELATED APPLICATION

This application is a continuation of application U.S. patent application Ser. No. 09/828,326, filed Apr. 5, 2001, now U.S. Pat. No. 6,750,061, which is a continuation of U.S. patent application Ser. No. 08/341,555, filed Jun. 24, 1996 now U.S. Pat. No. 6,271,037, which is a continuation-in-part of U.S. patent application Ser. No. 07/891,177, filed May 29, 1992, and is related to PCT/US93/05070 filed May 27, 1993. This application claims priority to each of the related applications and each of the related applications is incorporated by reference herein.

FIELD OF THE INVENTION

This invention relates to rapid and efficient methods for sequencing formed or forming polypeptides utilizing a mass spectrometer.

Polypeptides are a class of compounds composed of α-amino acid residues chemically bonded together by amide linkages with elimination of water between the carboxy group of one amino acid and the amino group of another amino acid. A polypeptide is thus a polymer of α-amino acid residues which may contain a large number of such residues. Peptides are similar to polypeptides, except that they are comprised of a lesser number of α-amino acids. There is no clear-cut distinction between polypeptides and peptides. For convenience, in this disclosure and claims, the term "polypeptide" will be used to refer generally to peptides and polypeptides.

Proteins are polypeptide chains folded into a defined three dimensional structure. They are complex high polymers containing carbon, hydrogen, nitrogen, and sulfur and are comprised of linear chains of amino acids connected by peptide links. They are similar to polypeptides, but of a much higher molecular weight.

For a complete understanding of physiological reactions involving proteins it is often necessary to understand their structure. There are a number of facets to the structure of proteins. These are the primary structure which is concerned with amino acid sequence in the protein chain and the secondary, tertiary and quaternary structures which generally relate to the three dimensional configuration of proteins. This invention is concerned with sequencing polypeptides to assist in determining the primary structure of proteins. It provides a facile and accurate procedure for sequencing polypeptides. It is also applicable to sequencing the amino acid residues at the termini of proteins.

Many procedures have been used over the years to determine the amino acid sequence, i.e. the primary structure, of polypeptides and proteins. At the present time, the best method available for such determinations is the Edman degradation. In this procedure, one amino terminal amino acid residue at a time is removed from a polypeptide to be analyzed. That amino acid is normally identified by reverse phase high performance liquid chromatography (HPLC), but recently mass spectrometric procedures have been described for this purpose (1) The Edman degradation cycle is repeated for each successive terminal amino acid residue until the complete polypeptide has been degraded. The procedure is tedious and time consuming. Each sequential removal of a terminal amino acid requires 20 to 30 minutes. Hence, with a polypeptide of even moderate length, say for example 50 amino acid residues, a sequence determination may require many hours. The procedure has been automated. The automated machines are available as sequenators, but it still requires an unacceptable amount of time to carry out a sequence analysis. Although the procedure is widely employed, one which required less time and which yielded information about a broader range of modified or unusual amino acid residues present in a polypeptide would be very useful to the art. A process which can be used to sequence individual members of mixtures of polypeptides would be particularly useful.

Recent advances in the art of mass spectroscopy have made it possible to obtain characterizing data from extremely small amounts of polypeptide samples. It is, for example, presently possible because of the sensitivity and precision of available instruments to obtain useful data utilizing from picomole to subpicomole amounts of products to be analyzed. Further, the incipient ion-trap technologies promise even better sensitivities, and have already been demonstrated to yield useful spectra in the $10^{-15}$ to $10^{-16}$ sample range.

In general, both electrospray and matrix-assisted laser desorption ionizaton methods mainly generate intact molecular ions. The resolution of the electrospray quadrupole instruments is about 1 in 2,000 and that of the laser desorption time-of-flight instruments about 1 in 400. Both techniques give mass accuracies of about 1 in 10-20,000 (i.e. +/−0.01% or better). There are proposed modifications of time-of-flight analyzer that may improve the resolution by up to factor of 10-fold, and markedly improve the sensitivity of that technique.

These techniques yield mass measurements accurate to +/−0.2 atomic mass units, or better. These capabilities mean that, by employing the process of this invention, the polypeptide itself whether already formed or as it is being formed can be sequenced more readily, with greater speed, sensitivity, and precision, than the amino acid derivative released by stepwise degradation techniques such as the Edman degradation. As will be explained in more detail below, the process of this invention employs a novel technique of sequence determination in which a mixture containing a family of "fragments", each differing by a single amino acid residue is produced and thereafter analyzed by mass spectroscopy.

SUMMARY OF THE INVENTION

This invention provides a method for the sequential analysis of polypeptides which may be already formed or are being formed by producing under controlled conditions, from the formed polypeptide or from the segments of the polypeptide as it is being formed, a mixture containing a series of adjacent polypeptides in which each member of the series differs from the next adjacent member by one amino acid residue. The mixture is then subjected to mass spectrometric analysis to generate a spectrum in which the peaks represent the separate members of the series. The differences in molecular mass between such adjacent members coupled with the position of the peaks in the spectrum for such adjacent members is indicative of the identity of the said amino acid residue and of its position in the chain of the formed or forming polypeptide.

The process of this invention which utilizes controlled cycling of reaction conditions to produce peptide ladders of predictable structure is to be contrasted with previous methods employing mass spectroscopy including exopeptidase digestion on uncontrolled chemical degradation. See references 2-5. Because of the uncontrolled nature of these previous methods, only incomplete sequence information could be obtained.

BRIEF DESCRIPTION OF THE DRAWINGS

FIG. 1 indicates a family or mixture of polypeptides (peptide ladder, as defined hereinafter) derived from a single formed polypeptide containing n amino acid residues. The mixture is analyzed in accordance with this invention to determine the amino acid sequence of the original polypeptide. Each amino acid in the sequence is denoted by a number with the numbering starting at the amino terminal of the peptide. X denotes a terminating group.

As will be explained in more detail below, FIGS. 8 through 10 are spectra obtained in the sequencing of a forming polypeptide employing the process of this invention.

The invention will be more easily understood if certain of the terms used in this specification and claims are defined.

The term "polypeptide" is used herein in a generic sense to describe both high and low molecular weight products comprising linear covalent polymers of amino acid residues. As the description of this invention proceeds, it will be seen that mixtures are produced which may contain individual components containing 100 or more amino acid residues or as few as one or two such residues. Conventionally, such low molecular weight products would be referred to a amino acids, dipeptides, tripeptides, etc. However, for convenience herein, all such products will be referred to as polypeptides since the mixtures which are prepared for mass spectrometric analysis contain such components together with products of sufficiently high molecular weight to be conventionally identified as polypeptides.

The term "formed polypeptide" refers to an existing polypeptide which is to be sequenced. It refers, for example to [$Glu^1$]fibrinopeptide B which is sequenced for purposes of illustration in Example 1. The process of the invention is, of course, most useful for sequencing the primary structure of unknown polypeptides isolated, for example, by reverse phase HPLC of an enzymatic digest from a protein.

The term "forming polypeptide" refers to such polypeptides as they are being formed for example by solid phase synthesis as illustrated in Example 2.

The term "peptide ladder" refers to a mixture containing a series of polypeptides produced by the processes described herein either from a formed or a forming polypeptide. As will be seen from the various figures and understood from this description of the invention, a peptide ladder comprises a mixture of polypeptides in which the various components of the mixture differ from the next adjacent member of the series by the molecular mass of one amino acid residue.

A "coupling reagents" is a reactant which forms a reaction product with a terminal amino acid residue of a polypeptide to be sequenced and is subsequently removed together with the residue.

A "terminating reagent" is a reactant which similarly forms a reaction product with a terminal amino acid of polypeptide and is stable to subsequent cycling procedures.

DETAILED DESCRIPTION OF THE INVENTION

There are several procedures for building peptide ladders, some applicable to the sequencing of formed polypeptides, others to sequencing of polypeptides as they are being formed.

Figure 3:
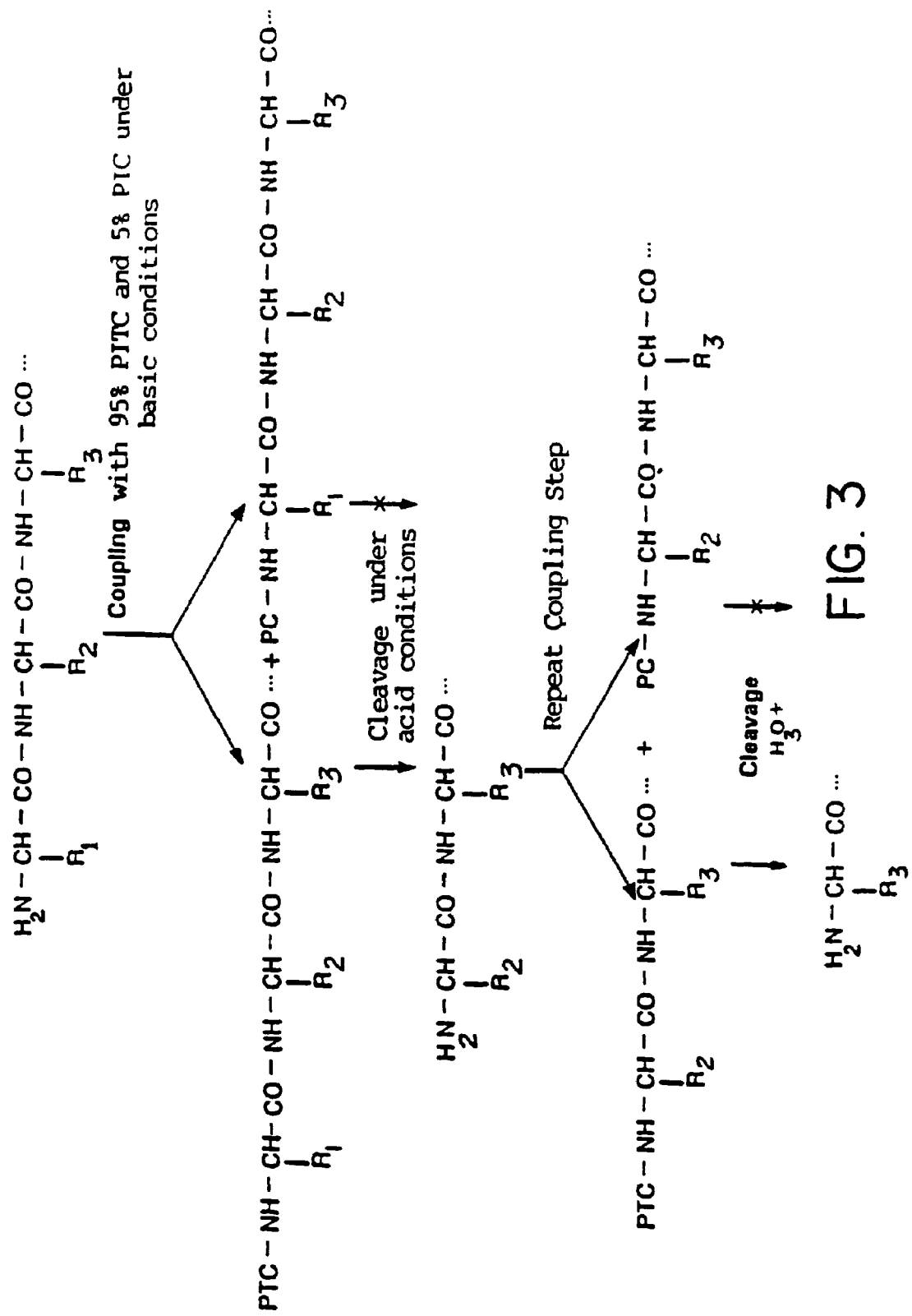
FIG. 3 shows the reactions involved in generating a peptide ladder from a formed polypeptide for analysis utilizing phenyl isothiocyanate (PITC) as the coupling reagent and phenyl isocyanate (PIC) as the terminating reagent.

One such process will be understood from a study of FIG. 3 which shows an embodiment of the invention which is applicable to formed polypeptides. The figure shows the sequencing of an original formed polypeptide which may contain any number of amino acid residues, even as many as 50 or more. The polypeptide is shown here by way of illustration as containing three residues, each residue with a side chain represented by $R_1$, $R_2$ or $R_3$ in accordance with conventional practice.

The significant feature of this embodiment of the invention, as illustrated in the figure, is that the reaction conditions are cycled to produce a peptide ladder in the final mixture. The final mixture is analyzed by mass spectroscopy to determine the exact mass of the components of the ladder, thereby to accumulate the information necessary to sequence the original polypeptide.

The skilled artisan will recognize that this procedure of sequencing a formed polypeptide makes use of degradation chemistry, but is based on a new principle, i.e. the original polypeptide is employed to generate a family of fragments, each differing by a single amino acid as shown in FIG. 1 wherein X represents a terminating agent. Typically X will be a terminating agent that is resistant to all subsequent reactions or manipulations in the cyclic degradation process of this invention. As will be described below, in connection with another embodiment of this invention, X may also be hydrogen.

In the process illustrated in FIG. 3, PITC is the coupling reagent and PIC is the terminating reagent. From such a family or peptide ladder of terminated molecular species prepared as outlined in the figure, the amino acid sequence can be simply read out in a single mass spectrometry operation, based on the mass differences between the intact molecular ions. Furthermore, because of the sensitivity of modern mass spectrometers, the accuracy of the amino acid sequence thus determined is unaffected, over a wide range (5-fold or more), by the amount of each molecular species present in the mixture.

Figure 2:
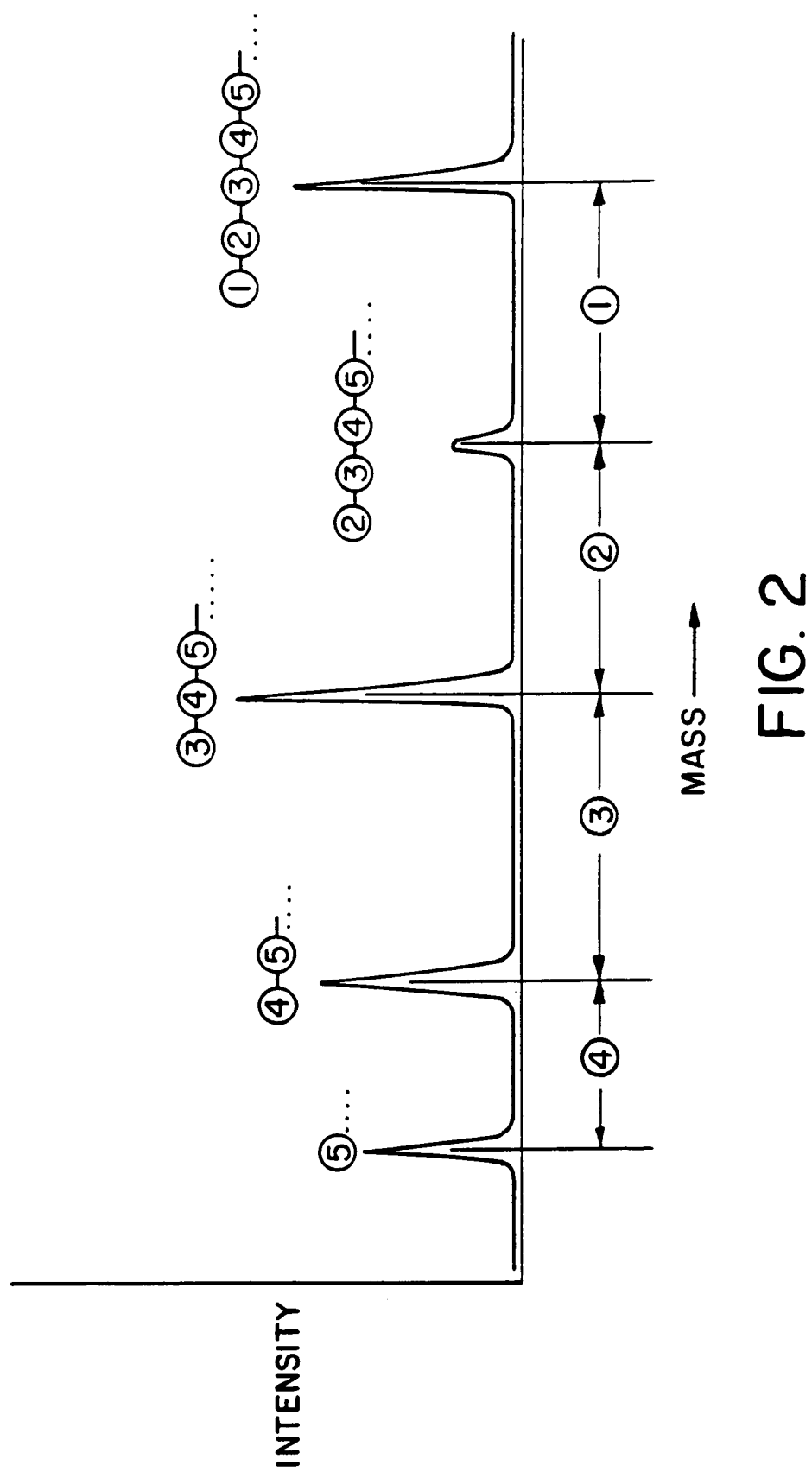
FIG. 2 is an idealized mass spectrum of the peptide ladder of a polypeptide similar to the family shown in FIG. 1.

FIG. 2 shows an idealized mass spectrum of a peptide ladder in which each peak is representative of one member of a series of terminated polypeptides each member of which differs from the adjacent member by one amino acid residue.

Thus, for example, if the peaks of the highest mass in FIG. 2 represent a polypeptide, the first five members of which at the amino terminal end may be:

Gly$^1$-Leu-Val-Phe-Ala$^5$- (SEQ ID NO:8), the next peak of lower mass would represent Leu$^2$-Val-Phe-Ala$^5$- (SEQ ID NO:9).

Subsequent peaks would represent products with one less amino acid residue. The difference in mass between adjacent members of the series would be indicative of the amino acid residue removed. The difference in molecular mass between the first product on the right and the adjacent product would correspond to a glycine residue. Subsequent peaks show the sequential removal of leucine, valine, phenylalanine and alanine residues thus establishing the sequence of these amino acid residues in the original polypeptide.

FIG. 3 illustrates a practical sequence of reactions by which the idealized procedure of FIGS. 1 and 2 can be conducted utilizing PITC and PIC as the reagents for sequencing an original formed polypeptide by cycling reaction conditions to produce a peptide ladder for spectrometric analysis.

In the first step of the sequencing procedure the original polypeptide is reacted with a mixture of PITC and PIC under basic conditions. A large molar excess of each reagent is employed. A much larger amount of PITC than of PIC is utilized so as to be certain that at each cycle of the procedure most of the available polypeptide reacts with the coupling agent but that a small measurable fraction of the available peptide reacts with the terminating reagent. The fraction reacted with the terminating agent will be determined by the relative activities of the coupling agent and the terminating agent, and the molar ratio of the two reagents.

The first reaction products which form during the basic step of the cycle comprise a mixture of original polypeptide terminated with PIC (PC-polypeptide) and an original polypeptide terminated with PITC (PTC-polypeptide). The PIC terminated polypeptide (PC-polypeptide) is stable or essentially stable under all subsequent reaction conditions with the result that it will be present in a measureable amount in the final mixture when that mixture is ready for analysis.

The next step in the procedure is to subject the PTC-polypeptide/PC-polypeptide mixture to acid conditions whereupon a reaction product separates from the PTC-polypeptide. This reaction product contains the terminal amino acid residue of the original peptide. The separation of this product results in the formation of a new polypeptide which, because the terminal amino acid has been cleaved contains one less amino acid than the original polypeptide.

The reaction mixture formed at the end of this cycle contains as the principal products:

1. unreacted coupling and terminating reagents,
2. a first reaction product which is the reaction product between the original polypeptide and the terminating reagent. It is a PC terminated polypeptide (PC-polypeptide).
3. a new polypeptide from which the amino terminal amino acid residue has been removed.

The skilled artisan will readily understand that sequential repeats of the cycle just described will result in the formation of a mixture which contains as the principal measureable components a series of PC-polypeptides each member of which contains one less amino acid residue than the next higher member of the series. The member of the series with the highest molecular mass will be the first reaction product between the original polypeptide and the terminating reagent. The molecular mass of each subsequent reaction product in the series will be the molecular mass of the next higher adjacent member of the series minus the molecular mass of the terminal amino acid residue removed by reaction with the PITC. The molecular mass of the PIC, blocking group or any other blocking group selected is irrelevant to the spectrometric analysis since the identity of each amino acid residue removed from the next adjacent peptide is determined by differences in molecular mass. These differences identify the amino acid residue, and the position of that mass difference in the spectrum data set defines the position of the identified residue in the original polypeptide.

A constant 5% termination of the available polypeptide at each cycle for ten cycles of the described chemistry would yield a peptide ladder in which the mole fraction of the original polypeptide after each cycle would be approximately

| FRACTION | MOLE |
|---|---|
| (X)-1-2-3-4-5-6-7-8-9-10-11-12- . . . -n-(OH) | .050 |
| (X)-2-3-4-5-6-7-8-9-10-11-12- . . . -n-(OH) | .048 |
| (X)-3-4-5-6-7-8-9-10-11-12- . . . -n-(OH) | .045 |
| (X)-4-5-6-7-8-9-10-11-12- . . . -n-(OH) | .043 |
| (X)-5-6-7-8-9-10-11-12- . . . -n-(OH) | .041 |
| (X)-6-7-8-9-10-11-12- . . . -n-(OH) | .039 |
| (X)-7-8-9-10-11-12- . . . -n-(OH) | .037 |
| (X)-8-9-10-11-12- . . . -n-(OH) | .035 |
| (X)-9-10-11-12- . . . -n-(OH) | .033 |
| (X)-10-11-12- . . . -n-(OH) | .031 |
| (X)-11-12- . . . -n-(OH) | .60 remains |

The differences in molecular mass between each successive member of the series in the peptide ladder can be readily determined with high precision by mass spectroscopy.

With relatively low molecular weight polypeptides, it is possible to repeat each cycle without removal of unreacted PITC or PIC. However, as illustrated in Example 1, it is generally preferred to remove unreacted coupling and terminating reagents at the completion of each cycle. Such removal may also include removal of the cleavage reaction product between the coupling reagent and the terminal amino acid.

Figure 4:
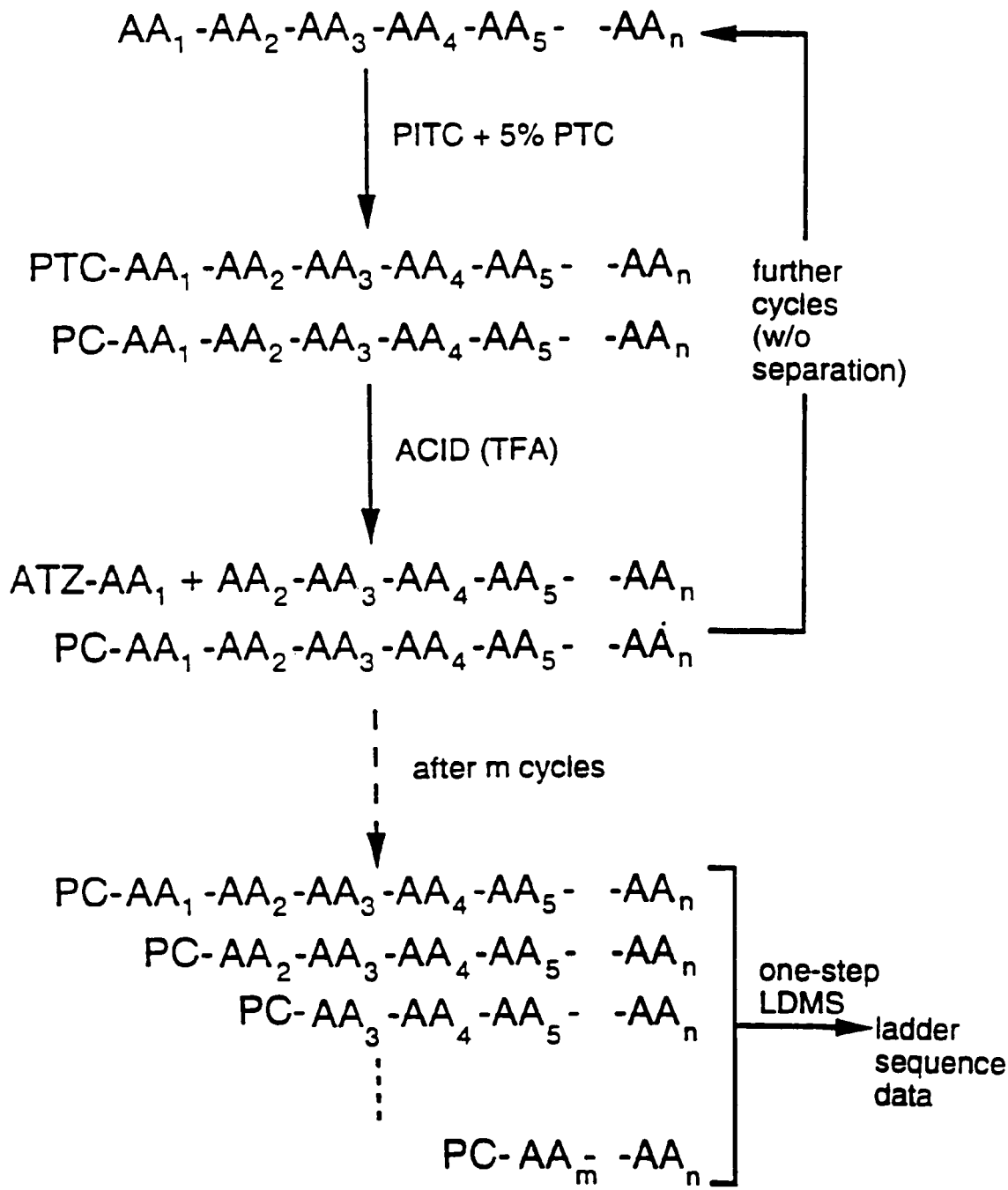
FIG. 4 is a more precise summary of the process shown in FIG. 3.
Figure 5:
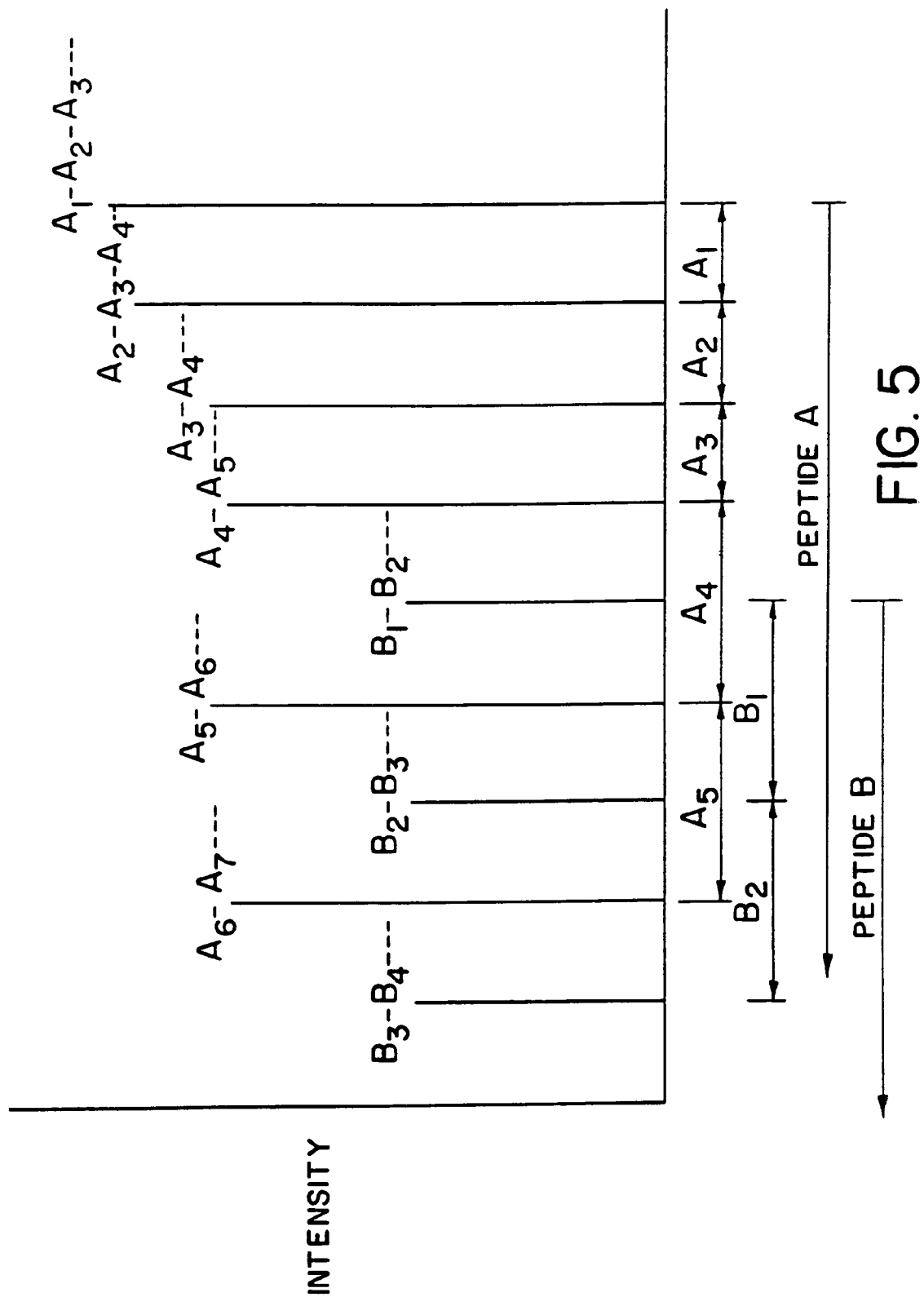
FIG. 5 is an idealized mass spectrum of peptide ladders obtained from a mixture of two formed polypeptides one of which is identified as A, the other as B.

FIG. 4 is a more precise summary of the procedure illustrated in FIG. 3 and described in detail above. It specifically illustrates the process utilizing a "one pot"

technique. In the figure "AA" stands for amino acid and ATZ represents 5-anilinothiazolinone. The other symbols have the same meaning as above.

The figure illustrates the preparation of a peptide ladder from a formed polypeptide using controlled ladder-generating chemistry. The stepwise degradation is conducted with a small amount of PIC and a major proportion of PITC. Successive cycles of peptide ladder generating chemistry are performed as described above without intermediate isolation or analysis of released amino acid derivatives. Finally the mixture containing the peptide ladder is read out in one step by laser desorption time-of-flight mass spectrometry (LDMS).

The coupling and terminating reagents are not limited to the pair described above. Those skilled in the art can readily select other equivalent reagents. Of course, the procedure can be adapted to either the amino terminal or the carboxy terminal of the polypeptide under analysis.

Another procedure for constructing a peptide ladder from a formed polypeptide is to conduct each cycle in a manner to insure incomplete termination. The process is similar to the above described procedure except that only a coupling reagent is employed and the peptide ladder comprises a series of polypeptides none of which is terminated with a terminating reagent but each of which differs from the adjacent member of the series by one amino acid residue. In this procedure, X of FIG. 1 is hydrogen. The principle of this embodiment of the invention is that only the coupling reagent is employed in the cycle, and the extent of reaction is limited for example by limiting reaction times so that all of the original formed polypeptide does not react. As a result, after the cycle has been moved to the acid step, the reaction mixture produced will contain:

1. Unreacted PITC,
2. The reaction product of PITC and the terminal amino acid residue with which it has reacted (PTC-polypeptide),
3. Unreacted original formed polypeptide,
4. A polypeptide with one less amino acid residue than the original polypeptide.

It will be apparent that by suitable adjustment of reaction conditions, continued repetition of the cycle any selected number of times will produce a desired peptide ladder similar to the ladder produced in the procedure which employs both coupling and terminating reagents except that the polypeptide members of the ladder are not end blocked with a terminating reagent. This process is similarly applicable to a mixture of polypeptides.

Another procedure for generating a peptide ladder with only one reagent involves termination by side reaction. In one such process, PITC is employed as a coupling reagent; and, under controlled conditions of oxidation, a small amount of PITC terminated polypeptide is converted to stable PIC terminated peptide to form a peptide ladder after a selected number of cycles. The key to this aspect of the invention is the controlled oxidation of a small amount of the PITC terminated polypeptide to form PIC terminated polypeptide which is stable, or essentially stable, under subsequent reactions conditions.

To describe the process with more specificity, the reaction steps are as follows:

1. React the polypeptide to be sequenced under basic conditions with an excess of PITC to convert substantially all of the polypeptide to PITC terminated polypeptide (PTC-polypeptide).
2. React the PTC-polypeptide with a controlled amount of oxygen to convert a small portion of the PTC-polypeptide, say 5%, to PC-polypeptide while leaving the balance unchanged.
3. Cycle the mixture to the acid step to cleave the PITC bound terminal amino acid from the PTC-polypeptide and leave a polypeptide with one less amino acid residue than the original polypeptide.
4. Repeat the cycle any selected number of times to generate a peptide ladder for mass spectrometric analysis.

A very significant practical advantage of the process of this invention is that it is possible to sequence a plurality of peptides in one reaction system. This advantage arises principally from the high degree of accuracy that is possible because of the recent advances in mass spectroscopy.

Figure 12A:
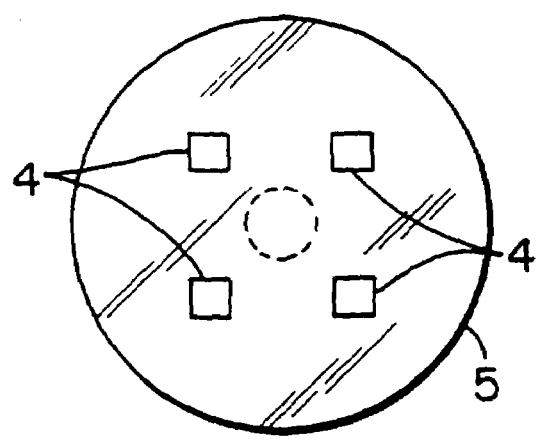
FIGS. 12A and 12B show the reaction support system employed in an embodiment of the inventions which permits multiple simultaneous sequencing of polypeptides.
Figure 12B:
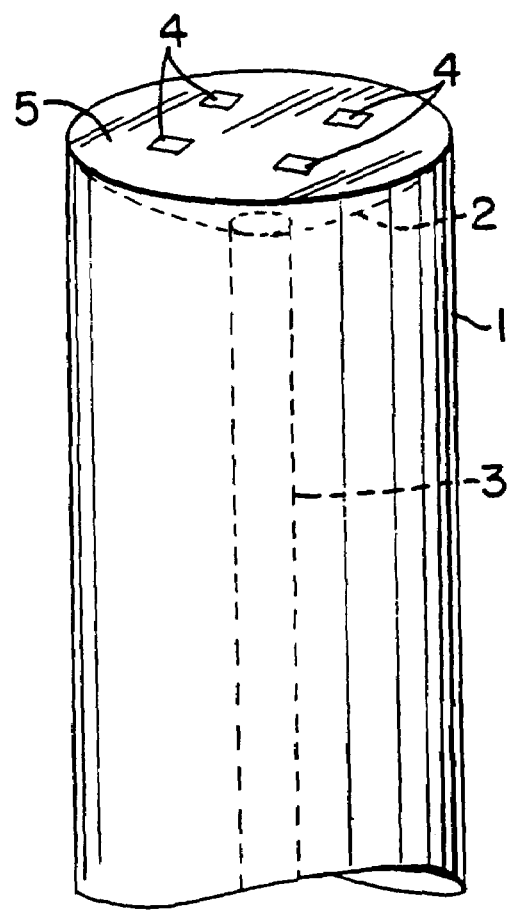

This aspect of the invention will be understood by reference to FIGS. 12A and 12B which show a suitable device for producing a plurality of peptide ladders. In the FIG. 1 is a reaction support member shown in the form of a cylinder with a holding basin 2 and a through bore 3 permitting the passage of chemicals. A series of absorbent members or discs 4, for example absorbent membranes are supported by a thin filter member 5 which may be simply a glass fiber or other suitable filter material.

In practice, the support member would be in a closed system adapted to permit the appropriate reactants for the preparation of a peptide ladder on each disc to contact each polypeptide to be sequenced. After each step of the cycle, the reactants exit the support member through the bore 3. The reactants are delivered to the reaction zone by any conventional pumping system of the type employed to collect reactants from a series of reservoirs, mix them and pass the mixture through a delivery nozzle.

Sequencing of formed polypeptides on samples immobilized on a solid support, as in the this embodiment of the invention is especially advantageous because it is applicable to very small amounts of total sample and because there are reduced handling losses and increased recoveries.

As applied to the system illustrated in the figures, any convenient number of polypeptides to be sequenced are separately absorbed on separate discs 4 which may be, for example, an absorbent membrane such as the cationic, hydrophilic, charge modified polyvinylidene fluoride membrane available from Millipore Corp. as Imobilon CD.

The discs are spaced apart on the filter paper 5 which is supported over the through bore 3 on support member 1 which is then placed in a closed system to conduct the controlled cyclic reactions appropriate to the production of a peptide ladder in accordance with this invention.

The amount of polypeptide absorbed on each segment may be as small as one picomole or even less. Generally, it is from about 1 to about 10 picomoles.

In a typical operation, 1 to 10 picomoles of each polypeptide are separately absorbed on the selected membrane discs and placed separately on the filter paper which is then placed on the support member as shown. The peptides are subjected to the PITC/PIC/base/acid cycle described above to generate a peptide ladder on each disc. Each separate peptide ladder containing mixture to be analyzed may be extracted from each separate membrane with an organic solvent containing a small amount of surfactant. One useful extraction solvent is 2.5% trifluoroacetic acid in a 1:1 mixture of acetonitrile and 1-O-n-octyl-β-glucopyranoside.

Figure 14:
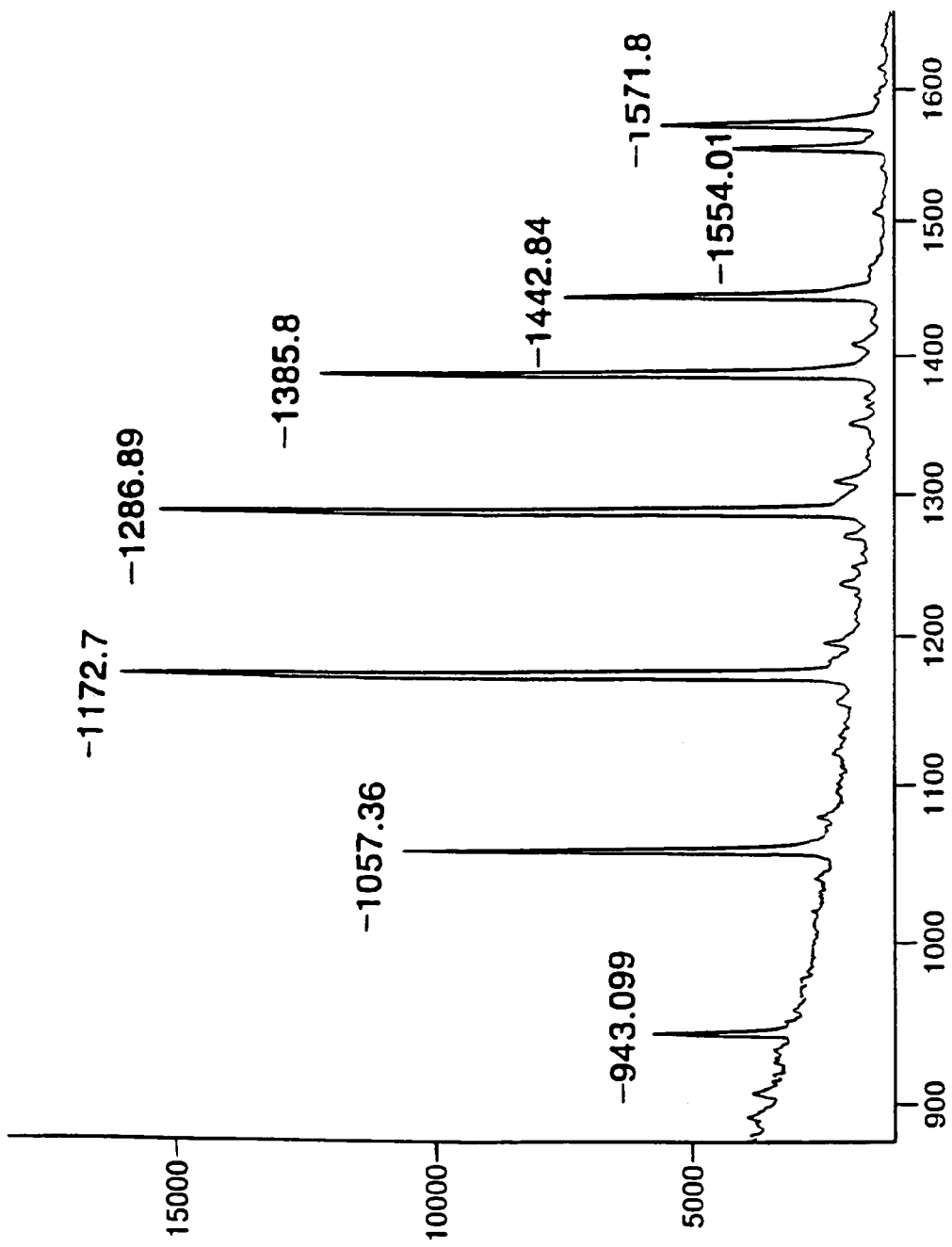
FIG. 14 shows the spectrum of a protein ladder generated by incomplete Edman degradation.

FIG. 14 shows the spectrum obtained using the absorbent membrane technology coupled with incomplete termination described above. To generate the peptide ladder which was analyzed, 50 picomoles of [Glu-1]fibrinopeptide B on Immobilon-CD membrane was applied to ABI-471A protein sequencer (Applied Biosystem). The sequencer was programmed using 5.5 minute cycle time with a cartridge temperature of 56° C. so as to insure incomplete reaction at each cycle. Six cycles were performed. Under these conditions, a reaction yield of about 56% was estimated. The resulting peptide ladder is comprised of free N-terminal amines.

This example illustrates the speed with which the sequencing can be performed. Similar spectra were obtained with a total loading of only 1 picomole of polypeptide on the membrane.

Although this multiple, simultaneous, sequence analysis of separate formed polypeptides utilizing the same chemical reagents for separate reactions with the said polypeptides has been specifically described by reference to the use of a mixture of specific coupling and terminating reagents in the same reaction zone, it will be apparent that the process is equally applicable to the other processes described above.

The system is, of course, applicable to the use of only one disc for the sequencing of a polypeptide or polypeptide mixture.

Although the discs are shown separately on the support, they may also be stacked or replaced with a column of suitably absorbent packing materials.

Further, there may be a number of support members in one device and the chemicals fed to the separate support members through a manifold system so that instead of only one reaction zone, there may be a plurality of reaction zones to still further increase the number of polypeptides which can be simultaneously sequenced.

An especially important embodiment of this invention is that it provides a method of locating covalent modifications on a polypeptide chain particularly post translational modifications of biologically important products which on chemical or enzymatic hydrolysis produce polypeptides which are phosphorylated, aceylated, glycosylated, cross-linked by disulfide bonds or otherwise modified. Such polypeptides are referred to in this specification and claims as "modified polypeptides".

The inability to directly identify, locate, and quantify modified amino acid residues such as phosphorylated residues in a modified polypeptide is a major shortcoming of standard sequencing methods, and has imposed major limitations on currently important areas of biological research, such as mechanisms of signal transduction. The process of this invention has general application to the direct identification of post-translation modifications present in a peptide chain being sequenced. A modified amino acid residue that is stable to the conditions used in generating the peptide ladder from a formed peptide reveals itself as an additional mass difference at the site of the covalent modification. As described above, from the mass difference, both the position in the amino acid sequence and the mass of the modified amino acid can be determined. The data generated can provide unambiguous identification of the chemical nature of the post translational modification.

Figure 13A:
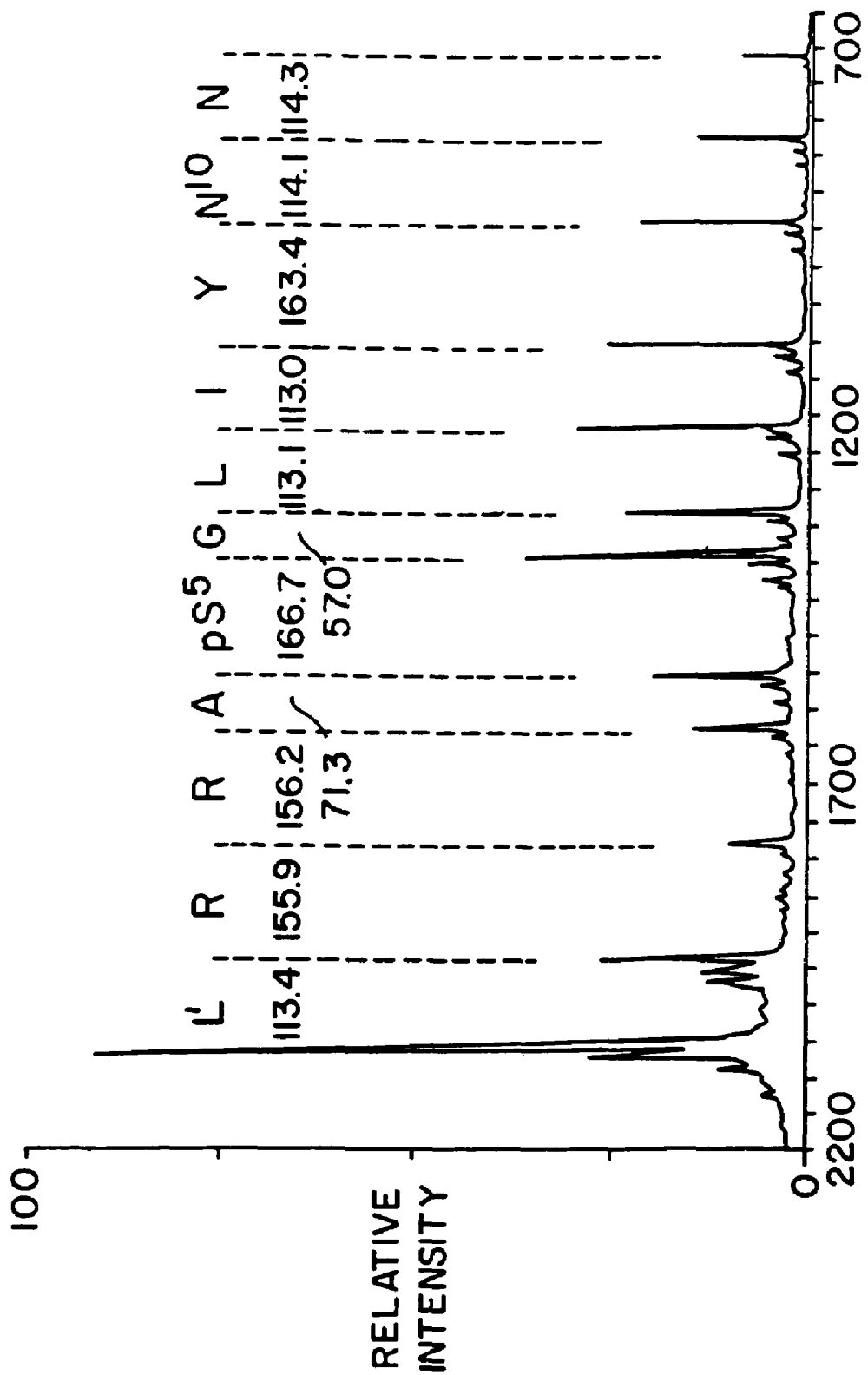
FIGS. 13A and 13B are the mass spectra of the peptide ladders formed from both phosphorylated (SEQ ID NO:5) (13A) and unphosphorylated (SEQ ID NO:6) (13B) 16 residue peptides containing a serine residue.
Figure 13B:
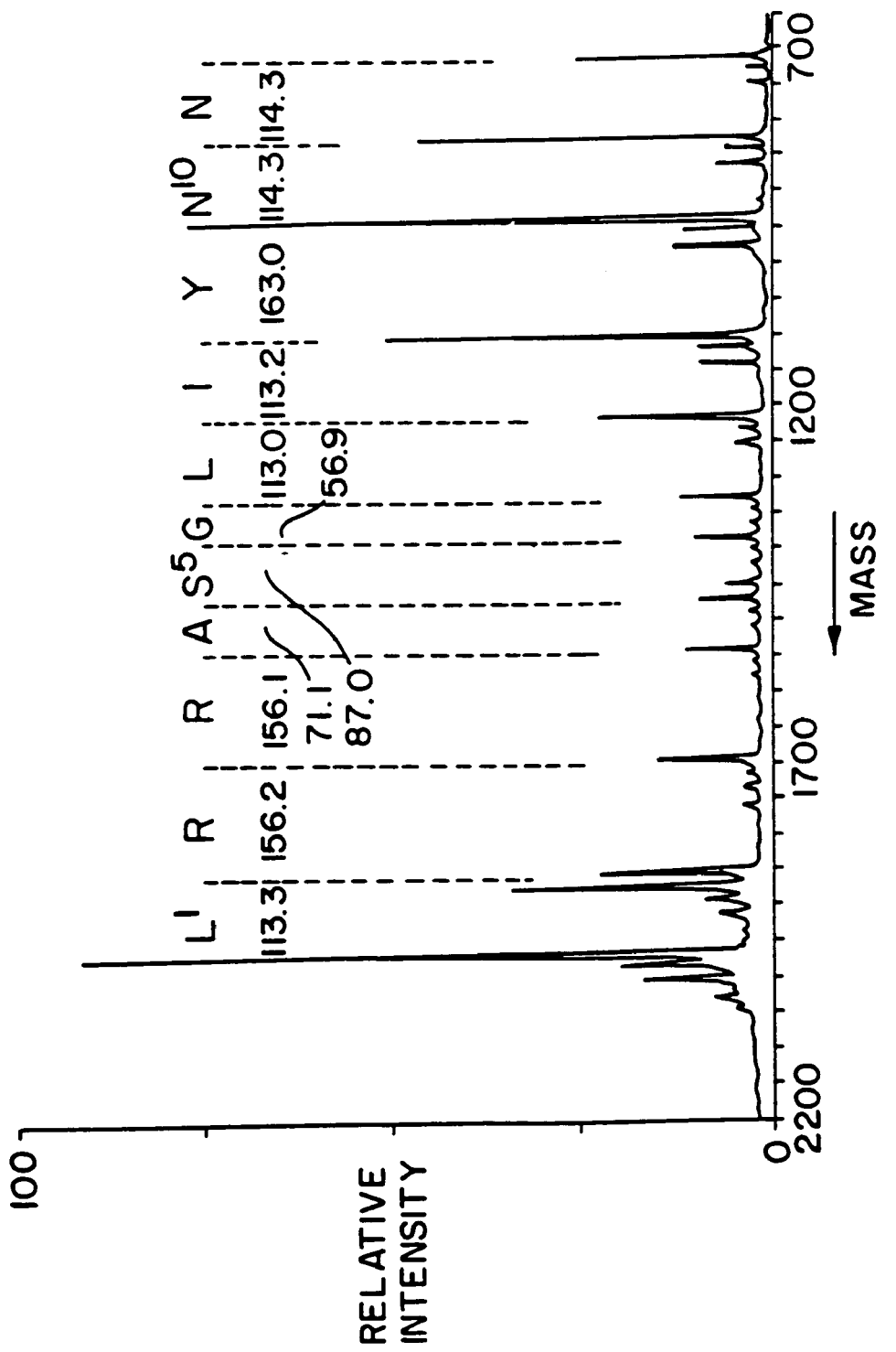

A typical example of this aspect of the invention is the analysis of both phosphorylated and unphosphorylated forms of the 16 residue peptide LRRASGLIYNNTLMAR-amide (SEQ ID NO:10) prepared by the method of Schnolzer et al (9) containing a phosphorylated serine residue prepared by enzymatic reaction using 3', 5'-cyclic AMP-dependent kinase. After ten cycles of PITC/PIC chemistry on each form of the peptide using the procedures described above and illustrated in Example 1, the two separate sequence-defining fragment mixtures (peptide ladders) were each read out by laser desorption mass spectrometry. The resulting protein ladder data sets are shown in FIGS. 13A and 13B. Again, the mass differences define the identity and order of the amino acids. For the phosphopeptide (FIG. 13A), a mass difference of 166.7 daltons was observed for the fifth amino acid from the N-terminal, compared with the mass difference of 87.0 for the same residue in the unphosphorylated peptide (FIG. 13B). This measured mass difference corresponds to a phosphyorylated serine residue, calculated mass 167.1 daltons. Thus, the protein ladder sequencing method has directly identified and located a Ser(Pi) at position five in the peptide. There was no detectable loss of phosphate from the phosphoserine residue, which has been regarded in the art as the most sensitive and unstable of the phosphorylated amino acids.

Altough only ten cycles of ladder generating chemistry were performed, sequence-defining fragments corresponding to eleven residues were observed, apparently arising from a small amount of premature cleavage (10). This side reaction which can have serious consequences for standard Edman methods, has no effect on the ladder sequencing approach.

A specific and very important advantage of this invention is that it is not limited to analysis of one polypeptide. Mixtures of polypeptides can be analyzed simultaneously in one reaction vessel. Each polypeptide will give a separate spectrum as shown in idealized form in FIG. 4. In this figure, the molecular masses of the original components of the mixture differ by any arbitrary mass difference. Each of the separate spectra can be analyzed as described above even though there may be appreciable overlapping in molecular mass among the polypeptides to be sequenced. This will be clear from the figure. As a result, it is possible to sequence proteins by analyzing mixtures of polypeptides obtained by chemical or enzymatic hydrolysis of the protein. The process can be outlined as follows:

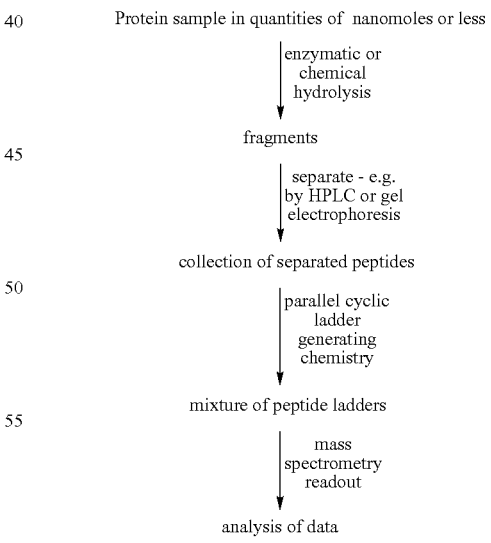

In most cases, gel electrophoresis will be employed to separate proteins and HPLC to separate polypeptides. Thus, for example, a protein mixture can be separated into its protein components by electrophoresis and each separate component sequenced by digestion into polypeptides, separation and ladder sequencing in accordance with the process of this invention to yield data from which the sequence of the entire protein can be deduced. The process of the invention may also be employed to obtain extensive data relating to the primary structure of intact proteins at their amino or carboxy terminals.

There follows a description of the application of this invention to a forming peptide.

Stepwise solid phase peptide synthesis involves the assembly of a protected peptide chain by repetition of a series of chemical steps (the "synthetic cycle") which results in the addition of one amino acid residue to an amino acid or peptide chain bound to a support, usually a rsin such as methylbenzhydrylamine. The final polypeptide chain is built up one residue at a time, usually from the C-terminal, by repetition of the synthetic cycle. As is well known to peptide chemists, the solid phase synthetic method does not always proceed according to plan. For any of a number of reasons, some of the polypeptide formed may terminate before the final product is produced. For example, a synthesis designed to produce a polypeptide containing twenty amino acid residues may produce as side products a variety of polypeptides containing lesser numbers of amino acid residues, e.g. tripeptides, octapeptides and dodecapeptides.

To utilize the advantages of this invention in solid phase synthesis, polypeptide-resin samples are collected after each cycle of amino acid addition. Mixing approximately equal amounts of all samples obtained in the course of a synthesis yields a peptide ladder containing all possible lengths of resin bound polypeptide. Cleavage of the resin from such a mixture produces a mixture of free polypeptide chains of all possible lengths containing a common carboxy or amino terminal. Usually, stepwise solid phase synthesis proceeds starting from the carboxy terminal. In these cases, the resulting peptide ladder will contain polypeptides all having a common carboxy terminal.

Consideration of the steps involved in the production of a heptapeptide will explain the procedure. If the heptapeptide to be produced is of the structure:

Ala$^1$-Val-Gly-Leu-Phe-Ala-Gly$^7$ (SEQ ID NO:11), the first synthetic step is the attachment of Gly to the resin, usually with a spacer molecule between the resin and the Gly. The next step is the attachment of N$^\alpha$-blocked Ala to the Gly following well known, coupling and deblocking procedures so that the synthesis is controlled. The cycle is repeated to form the heptapeptide on the resin from which it may be isolated by standard methods.

In accordance with the procedure of this invention, a small sample of polypeptide attached to resin is removed after each cycle. After completion of the synthesis, the seven samples are added together to produce a peptide ladder which contains the following components.

| | |
|---|---|
| Gly-Resin | |
| Ala-Gly-Resin | |
| Phe-Ala-Gly-Resin | |
| Leu-Phe-Ala-Gly-Resin | (SEQ ID NO:12) |
| Gly-Leu-Phe-Ala-Gly-Resin | (SEQ ID NO:13) |
| Val-Gly-Leu-Phe-Ala-Gly-Resin | (SEQ ID NO:14) |
| Ala-Val-Gly-Leu-Phe-Ala-Gly-Resin | (SEQ ID NO:15) |

The mixture is then treated, for example with hydrogen fluoride to generate a resin-free peptide ladder which is analyzed mass spectrometrically to assure that the final heptapeptide is of the desired amino acid structure.

One possible type of side reaction in stepwise solid phase synthesis is low level blocking at a particular residue (step) in the synthesis.

It will be apparent that each has occurred and mixed separate sample collected subsequent to the step at which a side reaction such as low level blocking has occurred above during the assembly of the final polypeptide will contain a portion of such terminated side product with the result that the amount of such terminated peptide is amplified in the final mixture as prepared for mass spectrometric analysis. Thus, for example, if for some reason such as low level blocking there was a termination of some polypeptide at the decapeptide stage in a synthesis designed to produce a 20-residue polypeptide, the sample from each subsequent synthetic cycle would contain terminated decapeptide and the final analytical sample would contain a 10-fold amplification of this side product. The information obtained by this method of analysis is very useful in designing optimum procedures for synthesizing polypeptides, especially those of high molecular weight. One adaptation of this invention to solid phase synthesis is illustrated in Example 2.

Optionally, the peptide resin samples collected as described above may be assayed calorimetrically, for example by a ninhydrin procedure to determine reaction yields prior to mixing to form a peptide ladder. This procedure provides a complimentary method of controlling and assessing the process.

In the foregoing process, a sample of polypeptide attached to the resin is collected at each step of the synthetic cycle for the preparation of the final analytical mixture. An alternative procedure for preparing the final sample is deliberate termination of a small portion of the forming peptide at each step of the synthetic cycle followed by removal of all of the peptides from the resin to form the analytical mixture directly.

This can be accomplished by utilizing, instead of one reversibly blocked amino acid residue at each step in the cycle, a mixture of the selected amino acid residue one portion of which is stable under the reaction conditions, another portion of which is susceptible to removal of the blocking group under controlled conditions.

If, for example, the amino acid residue to be added to the forming polypeptide is alanine, the peptide bond could be formed utilizing a mixture of Boc-alanine and Fmoc-alanine in which the carboxyl group is in the appropriate form for reaction, for example in the form of an hydroxybenzotriazole ester. After the peptide bond has been formed, one of the blocking groups, the removable group, can be removed under conditions such that the other blocking group remains intact. Repetition of this cycle will result in the formation of the desired polypeptide on the resin together with a peptide ladder comprising a series of polypeptides each member of which is joined to the resin and is terminated by the selected blocking group.

The procedure will be more readily understood by reference to the preparation of a specific polypeptide such as:

Gly$^1$-Phe-Ala-Leu-Ile$^5$ (SEQ ID NO:16).

The chemistry involved in the preparation of such pentapeptide is standard solid phase polypeptide synthesis applied in such a manner as to produce a peptide ladder. As applied to this invention, by way of example, the C-terminal amino acid residue would be joined to the resin, typically through a linker, as a mixture containing a major proportion of t-Boc-isoleucine and a minor proportion of Fmoc-isoleucine, e.g. in a 19:1 ratio.

The t-Boc blocking group is next removed with an acid such as trifluoroacetic acid. Since the Fmoc group is stable under acid conditions the Fmoc-isoleucine attached to the resin will retain its blocking group and will be stable to all subsequent reactions.

In the next step of this synthesis, a 19:1 mixture of Boc-leucine and Fmoc-leucine will be joined to the Ile-Resin, and the Boc blocking group selectively removed under acid conditions. As a result of this step in the synthetic cycle, the state of the resin may be indicated by:

Fmoc-Ile-Resin

Fmoc-Leu-Ile-Resin

Leu-Ile-Resin

Repetition of these reactions will result in a final resin mixture comprising a peptide ladder which may be represented by:

| | |
|---|---|
| Fmoc-Ile-Resin | |
| Fmoc-Leu-Ile-Resin | |
| Fmoc-Ala-Leu-Ile-Resin | |
| Fmoc-Phe-Ala-Leu-Ile-Resin | (SEQ ID NO:17) |
| Fmoc-Gly-Phe-Ala-Leu-Ile-Resin | (SEQ ID NO:18) |
| Gly-Phe-Ala-Leu-Ile-Resin | (SEQ ID NO:19) |

This peptide mixture is removed from the resin by standard solid phase procedures which, optionally, will also remove the Fmoc group to produce an analytical sample ready for analysis by mass spectroscopy as described above.

The peptide ladder can also be formed by the reverse procedure of employing Fmoc as the removable group and t-Boc as the terminating group.

Figure 11:
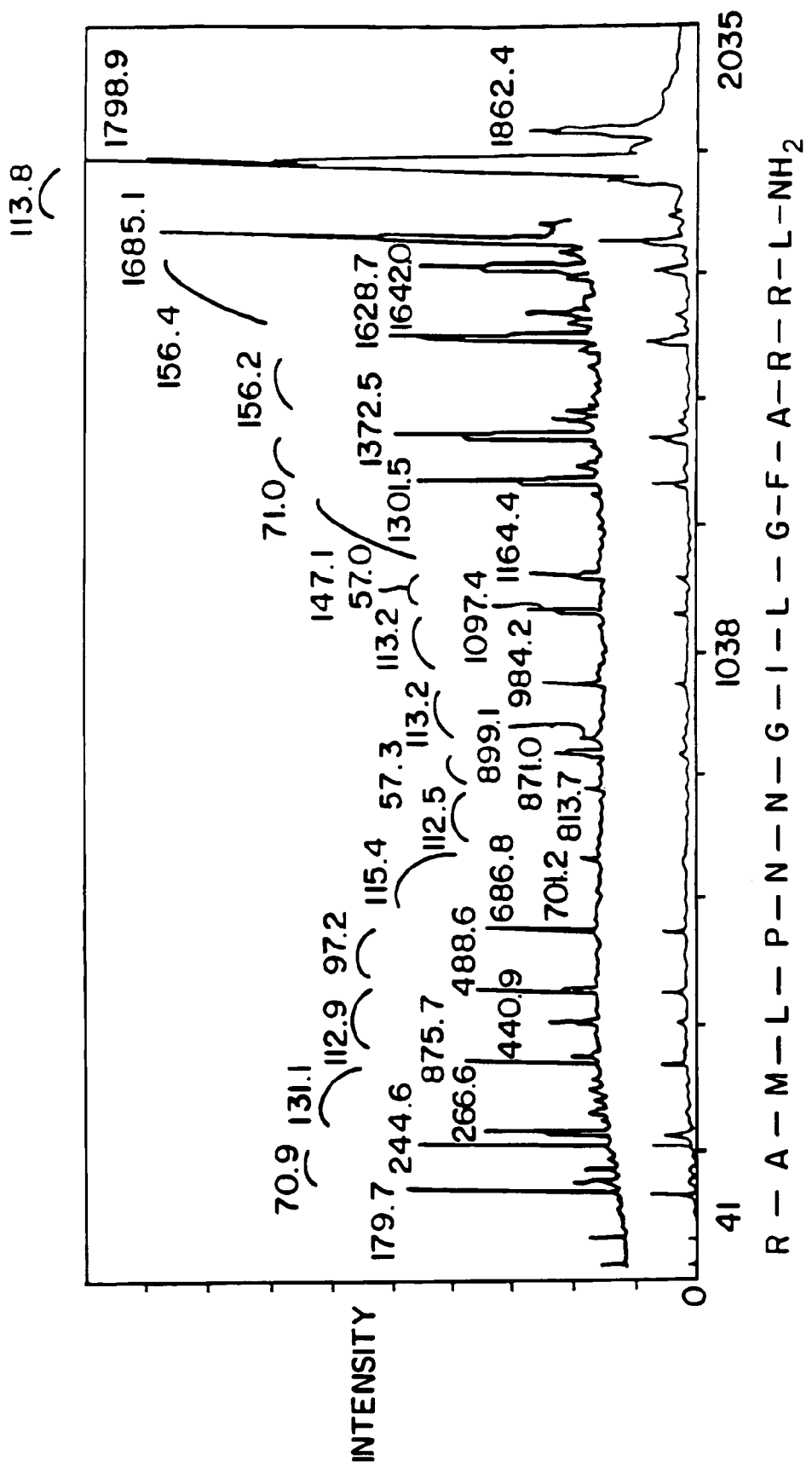
FIG. 11 is a spectrum of the reaction mixture (SEQ ID NO:4) obtained in Example 3.

The adaptation of this invention to solid phase synthesis techniques is illustrated in Example 3 and FIG. 11

Any blocking group stable to the conditions of chain assembly synthesis can be used in this application of the invention. For example, acetic acid could be added to each reversibly N-protected amino acid in a stepwise solid phase synthesis in an amount suitable to cause a few percent permanent blocking of the growing peptide chain at each step of the synthesis. The mass of the blocking group is without effect on the ability to read out the sequence of the peptide synthesized since the readout relies on mass differences between adjacent members of the polypeptide series as described above.

Using the procedures described, each individual resin bead carries the mixture of target full-length peptide and the peptide ladder. Typically each bead carries from 1 to 10 or more picomoles of polypeptides. Thus, cleavage of the products from a single bead permits the direct determination of the sequence of the polypeptide on that bead.

It is recognized that the foregoing procedures are described in an idealized form which does not include possible interference by other functional groups such as the hydroxyl group in tyrosine and serine, the "extra" carboxyl groups in dicarboxylic amino acids or the "extra" amino groups in dibasic amino acids. This method of description has been adopted to avoid unnecessarily lengthening the specification. The artisan will recognize the problems which will be introduced by the other functional groups and will know how to deal with them utilizing techniques well known to peptide chemists.

It will also be recognized that the procedures described have been applied to relatively small polypeptides. They are equally applicable to large polypeptides. For example, if the forming polypeptide is one which contains twenty or more amino acid residues, it may be expedient to sequence the pentapeptide, the decapeptide and the pentadecapeptide to be certain that the synthesis is going according to plan.

A variety of other chemical reaction systems can be employed to generate peptide ladders for analysis in accordance with this invention.

It will be recognized that there are a number of significant advantages to the processes of this invention. For example, the demands on yield of the chemical degradation reactions are much less stringent and more readily achieved than by wet chemical stepwise degradation techniques such as the Edman degradation in which low molecular weight derivatives are recovered and analyzed at each chemical step. Other advantages include accuracy, speed, convenience, sample recovery, and the ability to recognize modifications in the peptide such as phosphorylation. Relatively unsophisticated and inexpensive mass spectrometric equipment, e.g. time of flight; single quadrupole; etc. can be used.

By employing the process of this invention, it is routinely possible to sequence polypeptides containing 10 or more amino acid residues from one picomole, or even a smaller amount of a polypeptide in one hour or less including cyclic degradation, mass spectrometry, and interpretation.

The processes described may be readily automated i.e., carried out for example in microtiter plates, using an x, y, z chemical robot. Furthermore, the determination of amino acid sequence from mass spectrometric data obtained from the protein sequencing ladders is readily carried out by simple computer algorithms. The process of the invention therefore includes computer read-out of the spectra of the peptide ladders produced.

The skilled artisan will recognize that there are some limitations to the process of the invention as described above.

For example, some pairs of amino acids such as leucine and isoleucine have the same molecular weights. Therefore, they can not be distinguished by mass differences of terminated polypeptides in a series. There are several procedures for avoiding this difficulty. One is to differentiate them by cDNA sequencing. They are highly degenerate codons, so they can be accommodated by inosine substitution in DNA probes/primers for isolation/identification of the corresponding gene. This limitation will have little impact on practical application of the invention.

Further, several amino acids differ by only 1 amu. This places stringent requirements on accuracy of mass determination. However, this invention utilizes a determination of mass differences between adjacent peaks, not a determination of absolute masses. Since mass differences can be determined with great accuracy by mass spectroscopy, the limitation will also be of little practical significance.

Finally, samples which are blocked at the amino or carboxy terminal may not be susceptible to the generation of peptide ladders. This problem can be circumvented by chemical or enzymatic fragmentation of the blocked polypeptide chain to yield unblocked segments which can be separately analyzed.

The following non-limiting examples are given by way of illustration only and are not to be considered as limitations of the invention many apparent variations of which may be made without departing from the spirit or scope thereof.

EXAMPLE 1

Sequencing of [Glu$^1$]Fibrinopeptide B

Figure 7:
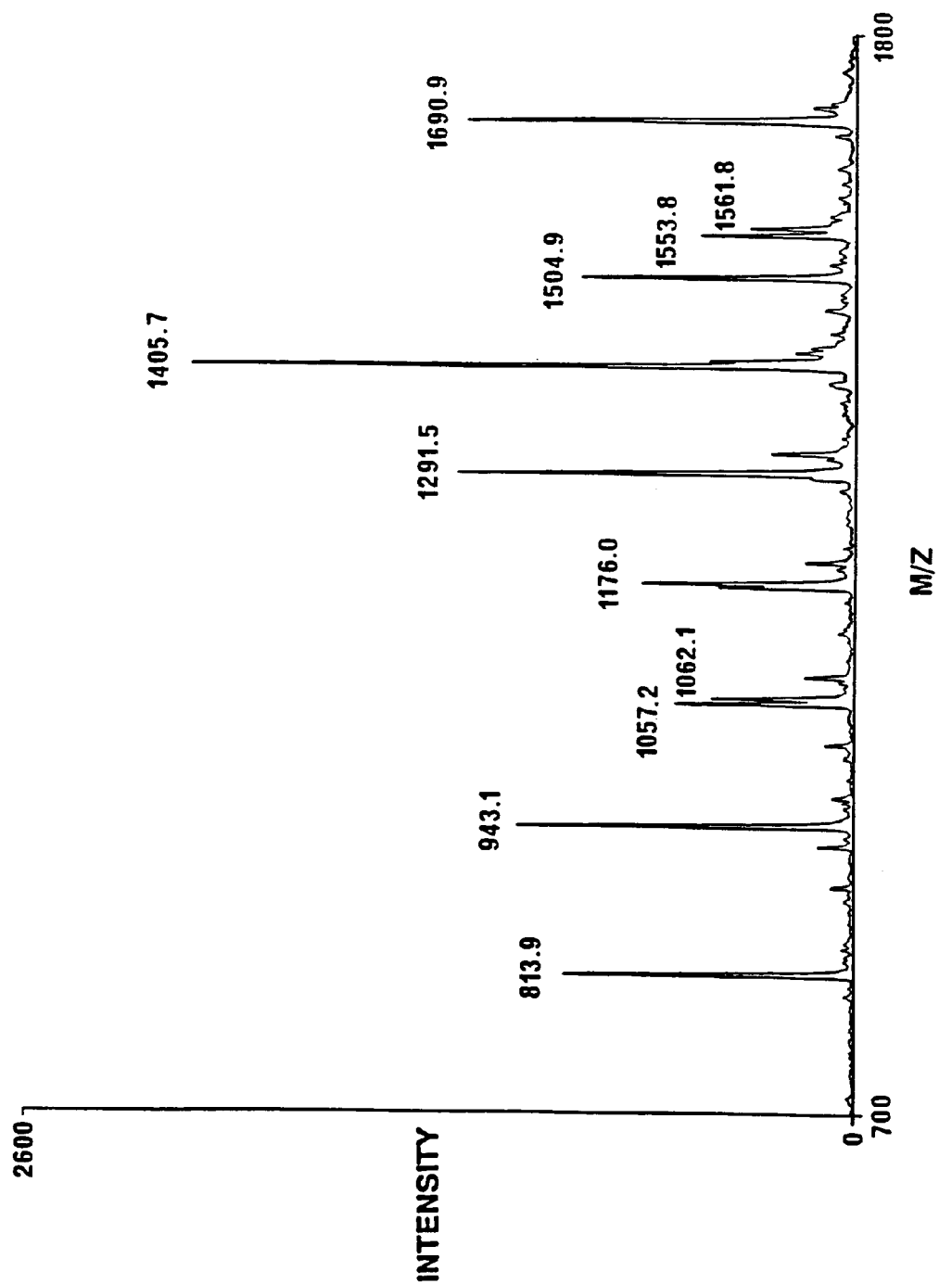
FIG. 7 is a positive ion matrix assisted laser desorption spectrum of [$Glu^1$]fibrinopeptide B after 7 cycles of sequential reactions in accordance with an embodiment this invention in which a formed polypeptide is degraded in a controled manner to produce a mixture containing a peptide ladder.

[Glu$^1$]Fibrinopeptide B was purchased from Sigma Chemical Co. (St. Louis, Mo.). The reported sequence was:

Glu¹-Gly-Val-Asn-Asp⁵-Asn-Glu-Glu-Gly-Phe¹⁰-Phe-Ser-Ala-Arg¹⁴ (SEQ ID NO:20). Matrix assisted laser desorption mass spectrometry gave MW 1570.6 dalton (Calculated: 1570.8 dalton) and showed high purity of the starting peptide. A mixture of PITC plus 5% v/v phenylisocyanate PIC was used in the coupling step. PIC reacts with the $NH_2$— of a polypeptide chain to yield an $N\alpha$-phenylcarbamyl-peptide which is stable to the conditions of the Edman degradation. A modification of a standard manual Edman degradation procedure (6) was used. All reactions were carried out in the same 0.5 mL polypropylene microfuge tube under a blanket of dry nitrogen. Peptide (200 pmoles to 10 nmole) was dissolved in 20 ul of pyridine/water (1:1 v/v; pH10.1); 20 uL of coupling reagent containing PITC:PIC:pyridine:hexafluoroisopropanol (20:1:76:4 v/v) was added to the reaction vial. The coupling reaction was allowed to proceed at 50° C. for 3 minutes. The coupling reagents and non-peptide coproducts were extracted by addition of 300 uL of heptane:ethyl acetate (10:1 v/v), gentle vortexing, followed by centrifugation to separate the phases. The upper phase was aspirated and discarded. This washing procedure was repeated once, followed by washing twice with heptane:ethyl acetate (2:1 v/v). The remaining solution containing the peptide products was dried on a vacuum centrifuge. The cleavage step was carried out by addition of 20 uL of anhydrous trifluoroacetic acid to the dry residue in the reaction vial and reaction at 50° C. for 2 minutes, followed by drying on a vacuum centrifuge. Coupling-wash-cleavage steps were repeated for a predetermined number of cycles. The low MW ATZ/PTH derivatives released at each cycle were not separated/analyzed. Finally, the total product mixture was subjected to an additional treatment with PIC to convert any remaining unblocked peptides to their phenylcarbamyl derivatives. In this final step, the sample was dissolved in 20 uL of trimethylamine/water (25% wt/wt) in pyridine (1:1 v/v); 20 uL of PIC/pyridine/HFIP (1:76:4 v/v) was added to the reaction vial. The coupling reaction was carried out at 50° C. for 5 min. The reagents were extracted as described above. After the last cycle of ladder generating chemistry, the product mixture was dissolved in 0.1% aqueous trifluoroacetic acid:acetonitrile (2:1, v/v). A 1 uL aliquot (250 pmol total peptide, assuming no losses) was mixed with 9 uL of $\alpha$-cyano-4-hydroxy-cinnanimic acid (5 g/L in 0.1% trifluoroacetic acid: acetonitrile, 2:1 v/v), and 1.0 uL of this mixture of total peptide products (25 pmol) and matrix was applied to the probe tip and dried in a stream of air at room temperature. Mass spectra were acquired in positive ion mode using a laser desorption time-of-flight instrument constructed at The Rockefeller University (7). The spectra resulting from 200 pulses at a wavelength of 355 nm, 15 mJ per pulse, were acquired over 80 seconds and added to give a mass spectrum of the protein sequencing ladder shown in FIG. 7. Masses were calculated using matrix peaks of known mass as calibrants.

Figure 6:
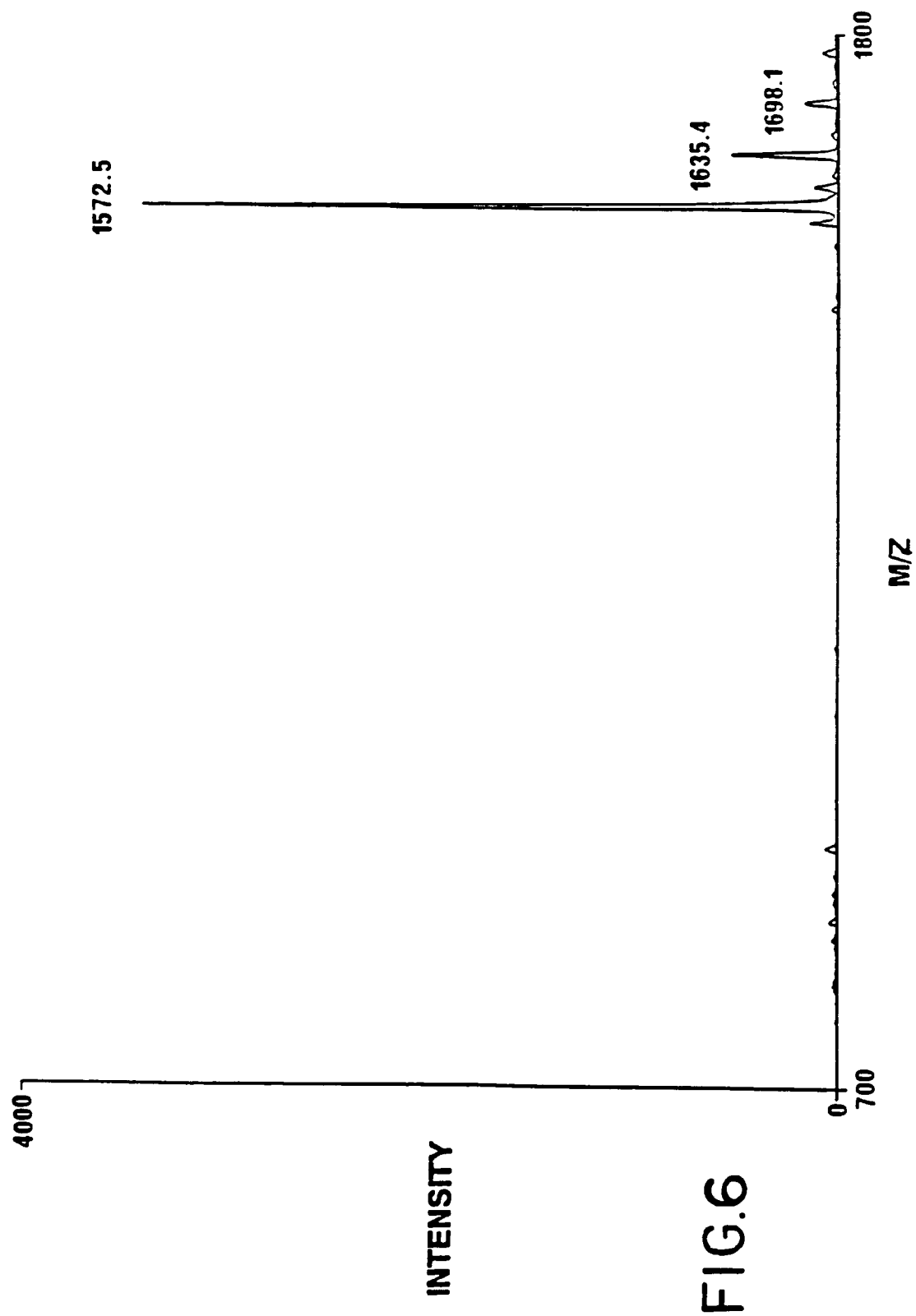
FIG. 6 is a positive ion, matrix assisted laser desorption mass spectrum of the formed polypeptide [$Glu^1$]fibrinopeptide B.

Peptide sequence read-out. Positive ion (MALDMS) spectra of [Glu¹]Fibrinopeptide B is shown in FIG. 6. A protonated molecular ion [M+H] was observed at m/z 1572.5 (calculated value is 1571.8).

Its positive ion MALDMS spectrum of the reaction mixture obtained after seven cycles is shown in FIG. 6. Each of the peaks in the spectrum represents a related phenylcarbamoylpeptide derivative in the peptide ladder (except a few peaks which will discussed later). The amino acid sequence can be easily read-out from the mass difference of adjacent two peaks for instance, the mass difference are 129.1, 56.9, and 99.2 between peaks at m/z 1690.9 and 1561.8, peaks at m/z 1561.8 and 1504.9 and peaks at m/z 1504.9 and 1405.7. Which correspond to glutamic acid (ca. 129.12), glycine (ca. 57.05) and valine (ca. 99.13) residues, respectively. One set of paired peaks gives mass difference 119.0 (1062.1-943.1) which corresponds to the phenylcarbamoyl group. In other words, these two peaks represent one piece of peptide with or without phenylcarbamoyl group. Peak at m/z 1553.8 corresponds partially blocked peptide with pyroglutamic acid at the N-terminus. This results from cyclization of the N-terminal Glu under the reaction conditions used. Such products are readily identified from the accurately measured mass and know chemical reaction tendencies.

EXAMPLE 2

Stepwise solid phase synthesis of the 99 amino acid residue polypeptide chain corresponding to the monomer of the HIV-1 protease (SF2 isolate):

```
PQITLWQRPLVTIRIGGQLKEALLDTGADDTVLEEMNLPGKWKPKMIGGI

GGFIKVRQYDQIPVEI (Aba) GHKAIGTVLVGPTPVNIIGRNLLTQIG (Aba) TLNF⁹⁹ (SEQ ID NO:21)
```

[where Aba=$\alpha$-amino-n-butyric acid] was undertaken.

Highly optimized Boc-chemistry instrument-assisted stepwise assembly of the protected peptide chain was carried out on a resin support, according to the method described by S. B. H. Kent (8). Samples (3-8 mg, about 1 umole each) were taken after each cycle of amino acid addition. The protected peptide-resin samples were mixed in three batches of consecutive samples: (number corresponds to the amino acid after which sample was taken, i.e. residue number in the target sequence.) 99-67; 66-33; 32-1. The first such mixture contained the peptides:

```
                       99-Resin
                    98-99-Resin
                 97-98-99-Resin
              96-97-98-99-Resin
              . . . (etc.) . . .
       70 . . . 96-97-98-99-Resin
    69-70 . . . 96-97-98-99-Resin
 68-69-70 . . . 96-97-98-99-Resin
67-68-69-70 . . . 96-97-98-99-Resin
```

Similarly for the other two mixtures. The mixed batches of peptide-resin were deprotected and cleaved with HF (1 hours, at 0° C., plus 5% cresol/5%/thiocresol). The products were precipitated with diethyl ether, dissolved in acetic acid-water 950/50%, v/v) and then lyophilized.

Figure 8:
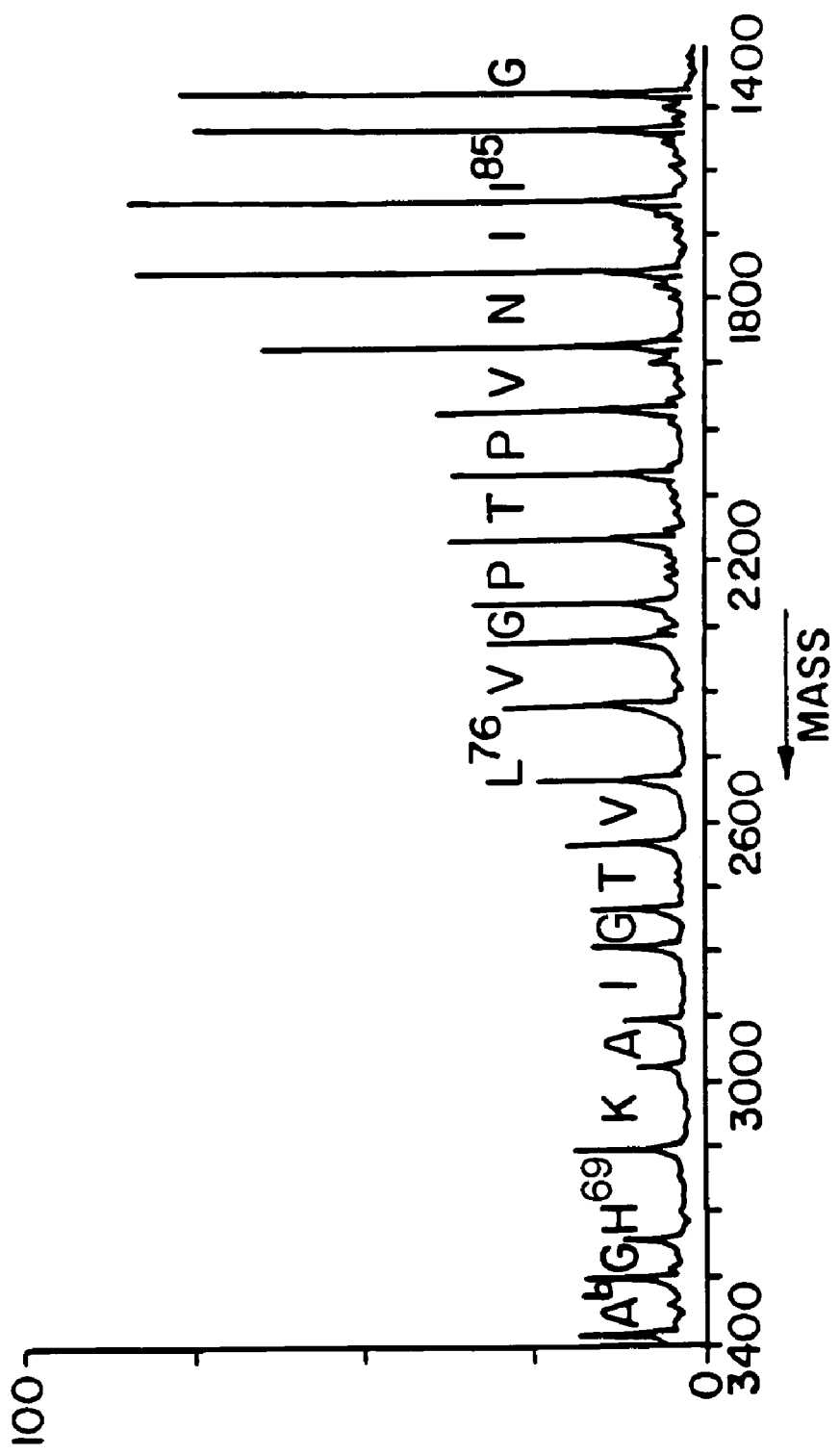
FIG. 8 is the spectrum of the peptide ladder (SEQ ID NO:1) in the region 87-67 obtained from the mixture 99-67 in Example 2.

Each peptide mixture was dissolved in 0.1% TFA, 1 uL of the peptide mixture (10 uM per peptdie component) was added to 9 uL of 4-hydroxy- -cyanocinnamic acid in a 1:2 (v/v) ratio of 30% acetonitrile/0.1% aqueous trifluoroacetic acid. 0.5 uL of the resulting mixture was applied to the mass spectrometer probe and inserted into the instrument (7). The spectra shown in FIGS. 8 and 9 are the result of adding the data of each of 100 laser shots performed at a rate of 2.5 laser shots/second. FIG. 8 shows the mass spectrum obtained from the mixture resulting from cleaving mixed samples from residues 99-67 of the synthesis. FIG. 9 shows the mass spectrum obtained from the mixture resulting from cleaving mixed samples from residues 66-33 of the synthesis. Table 1 shows the measured mass differences between consecutive peaks of a selection of these peaks and compares them with the mass differences calculated from known sequences of the target peptides. The agreements are sufficiently close to allow confirmation of the correctness of the synthesis.

Figure 9A:
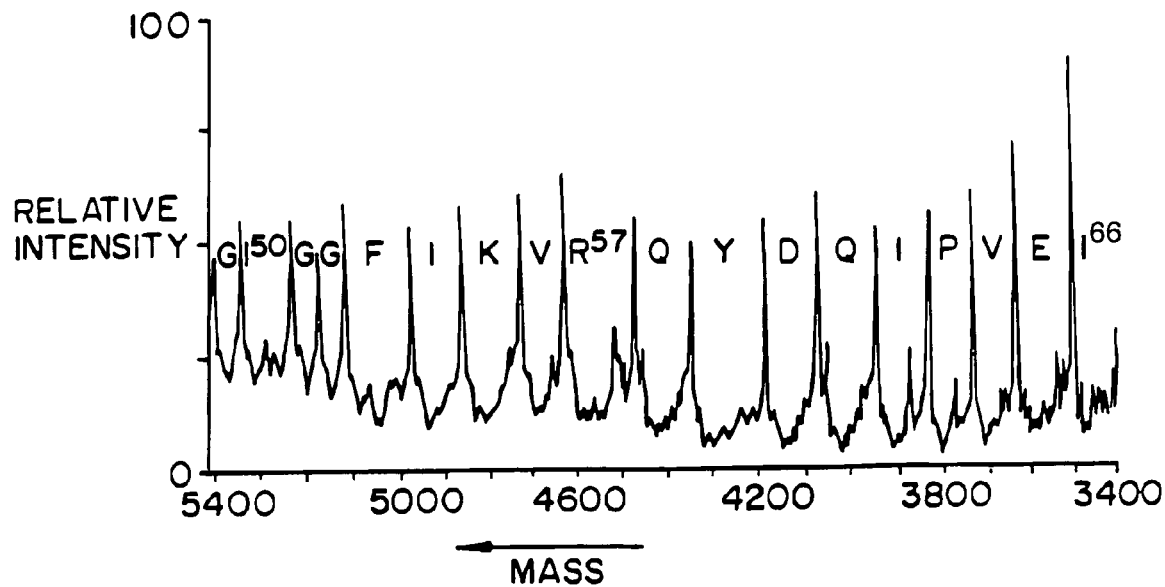
FIG. 9 (a and b) is the spectrum of the mixture 66-33 (SEQ ID NOS: 2 and 3) obtained in Example 2.
Figure 9B:
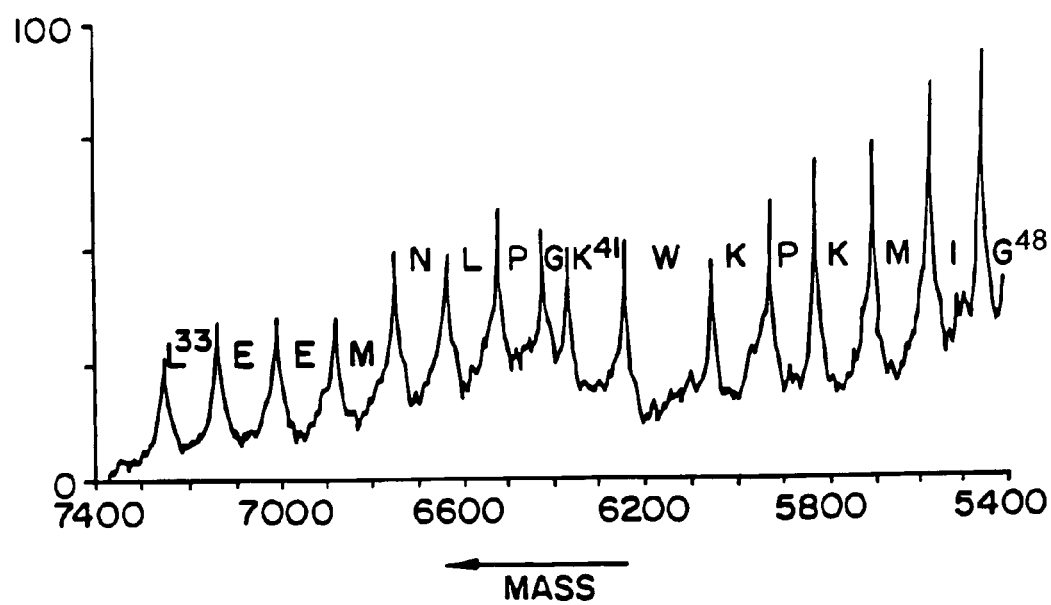

FIGS. 9A and 9B show mass spectra of the mixture obtained from mixed samples from residues (66-33) of the synthesis.

The sequence of the assembled polypeptide chain can be read out in a straightforward fashion from the mass differences between consecutive peaks in the mass spectra of the peptide mixture. This confirmed the sequence of amino acids in the peptide chain actually synthesized. The identity of the amino acids as determined by such mass differences is shown in Table 1 (SEQ ID NO:22).

TABLE 1

The identify of amino acid by the mass differences in protein ladder sequencing using matrix-assisted laser desorption mass spectrometry.

| Amino Acid | Mass Difference (Measured, Da) | Deviation | Amino Acid | Mass Difference (Measured, Da) | Deviation |
|---|---|---|---|---|---|
| $Leu^{33}$ | 113.3 | 0.1 | $Asp^{60}$ | 114.8 | −0.3 |
| $Glu^{34}$ | 129.7 | 0.6 | $Gln^{61}$ | 128.7 | 0.6 |
| $Glu^{35}$ | 129.5 | 0.4 | $Ile^{62}$ | 113.2 | 0.0 |
| $Met^{36}$ | 130.8 | −0.4 | $Pro^{63}$ | 97.0 | −0.1 |
| $Asn^{37}$ | 115.0 | 0.9 | $Val^{64}$ | 99.4 | 0.3 |
| $Leu^{38}$ | 112.4 | −0.8 | $Glu^{65}$ | 128.6 | −0.5 |
| $Pro^{39}$ | 97.9 | 0.8 | $Ile^{66}$ | 113.3 | 0.1 |
| $Gly^{40}$ | 56.1 | −0.9 | $Aba^{67}$ | 84.9 | −0.2 |
| $Lys^{41}$ | 128.1 | 0.0 | $Gly^{68}$ | 57.0 | 0.0 |
| $Trp^{42}$ | 186.4 | 0.2 | $His^{69}$ | 137.3 | 0.2 |
| $Lys^{43}$ | 128.2 | 0.0 | $Lys^{70}$ | 127.8 | −0.4 |
| $Pro^{44}$ | 97.1 | 0.0 | $Ala^{71}$ | 71.4 | 0.3 |
| $Lys^{45}$ | 128.0 | −0.2 | $Ile^{72}$ | 113.4 | 0.2 |
| $Met^{46}$ | 131.9 | 0.7 | $Gly^{73}$ | 56.8 | −0.2 |
| $Ile^{47}$ | 112.6 | −0.6 | $Thr^{74}$ | 101.1 | 0.0 |
| $Gly^{48}$ | 57.9 | 0.9 | $Val^{75}$ | 99.2 | 0.1 |
| $Gly^{49}$ | 56.3 | −0.7 | $Leu^{76}$ | 113.1 | −0.1 |
| $Ile^{50}$ | 112.4 | −0.8 | $Val^{77}$ | 99.1 | 0.0 |
| $Gly^{51}$ | 57.6 | 0.6 | $Gly^{78}$ | 57.1 | 0.1 |
| $Gly^{52}$ | 57.5 | 0.5 | $Pro^{79}$ | 97.2 | 0.1 |
| $Phe^{53}$ | 147.3 | 0.1 | $Thr^{80}$ | 101.1 | 0.0 |
| $Ile^{54}$ | 112.5 | −0.7 | $Pro^{81}$ | 97.1 | 0.0 |
| $Lys^{55}$ | 128.9 | 0.8 | $Val^{82}$ | 99.2 | 0.1 |
| $Val^{56}$ | 99.0 | −0.1 | $Asn^{83}$ | 113.8 | −0.3 |
| $Arg^{57}$ | 156.2 | 0.0 | $Ile^{84}$ | 113.4 | 0.2 |
| $Gln^{58}$ | 128.4 | 0.3 | $Ile^{85}$ | 113.1 | 0.0 |
| $Tyr^{59}$ | 162.6 | −0.6 | $Gly^{86}$ | 57.1 | 0.0 |

Figure 10:
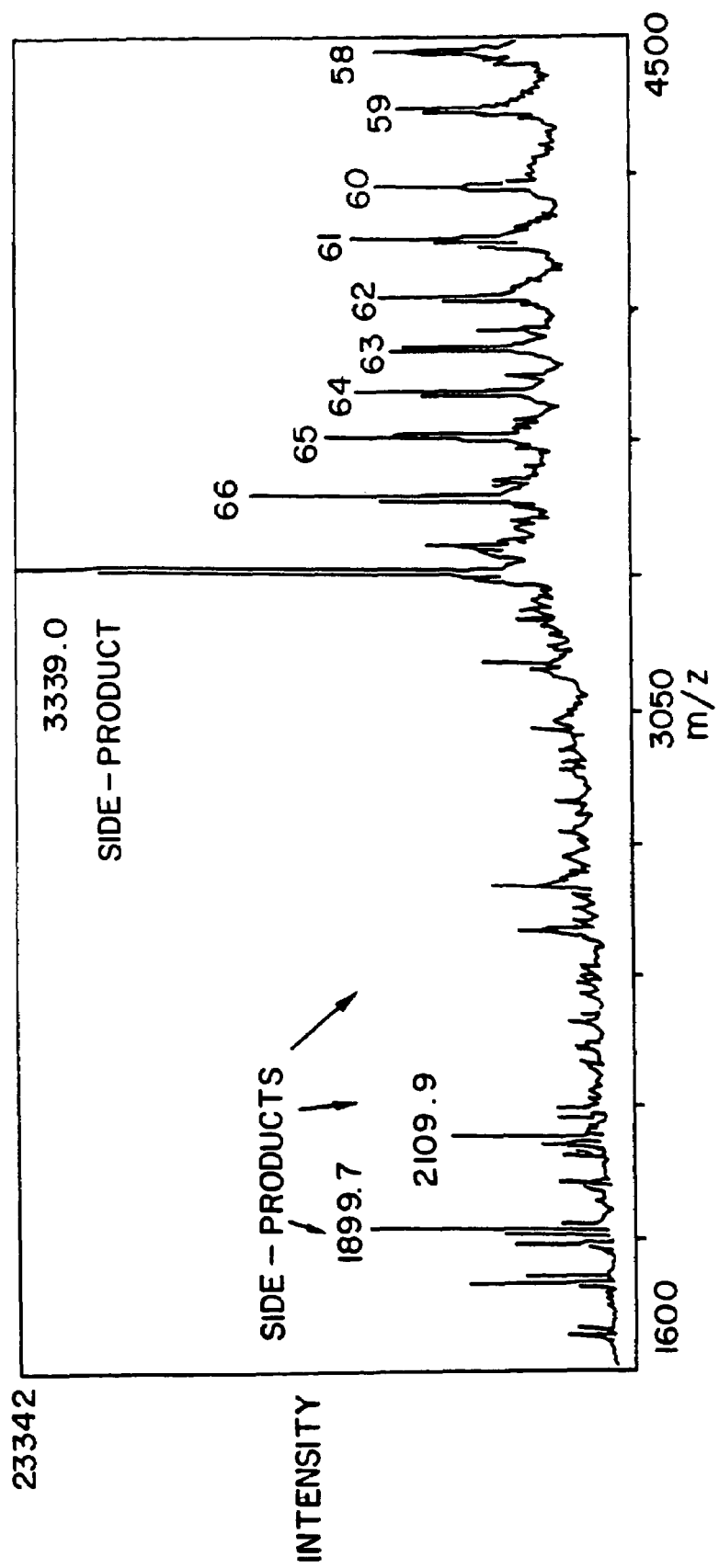
FIG. 10 is a spectrum of the low mass region obtained from the mixture 66-33 obtained in Example 2 showing the side reaction products formed during the synthesis of HIV-1 protease.

In addition, terminated by-products (where the peptide chain has become blocked and does not grow anymore) are present in every peptide-resin sample taken after the step in which the block occurred. Thus, there is an amplification factor equal to the number of resin samples in the batch after the point of termination. This can be seen in FIG. 10 (samples #66-33) which contains a peak at 3339.0. This corresponds to the peptide 71-99, 3242.9 (N-terminal His71) plus 96.1 dalton. The characteristics mass, together with knowledge of the chemistry used in the synthesis identifies the blocking group as $CF_3 CO$-(97.1-H=96.1 dalton). The observed by product is the trifluoroacetyl-peptide, $N\alpha$-Tfa-(71-99). The ratio of the amount of this component to the average amount of the other components is about 2:1. There were 34 samples combined in this sample. Thus, the terminated byproduct $N\alpha$-Tfa-(71-99) had occurred at a level of about 5 mol %. This side reaction, specific to the N-terminal His-peptide chain, has not previously been reported. This illustrates the important sensitivity advantage provided by this amplification effect in detecting terminated peptides. Such byproducts are not readily detected by any other means.

EXAMPLE 3

Boc/Fmoc Terminations

Synthesis of the peptide LRRAFGLIGNNPLMAR-amide (SEQ ID NO:23) was performed manually on a 0.2 mmol scale using p-methylbenzhydrylamine resin and 0.8 mmoles amino acid (95 mol % $N-\alpha$-Boc, 5 mol % $N-\alpha$-Fmoc) according to the in situ neutralization methods of Schnolzer et al (9). The following side chain protecting groups were used: Boc-Arg, tosyl; Fmoc-Arg, 2,3,6-trimethyl-4-methoxybenzenesulfonyl (Mtr). Fmoc-Arg(Mtr) was used for its greater stability in trifluoroacetic acid (TFA). After completion of the chain assembly, Fmoc groups were removed using 50% piperidine/DMF, followed by Boc group removal in TFA. The peptide fragments were then cleaved from the resin by treatment with HF-10% p-cresol (0° C., 1 hour). The resulting crude peptide products were precipitated and washed with ether, dissolved in 50% acetic acid, diluted with water and lyophilized. The mass spectra of the reaction mixture thus produced is shown in FIG. 11.

EXAMPLE 4

Figure 15:
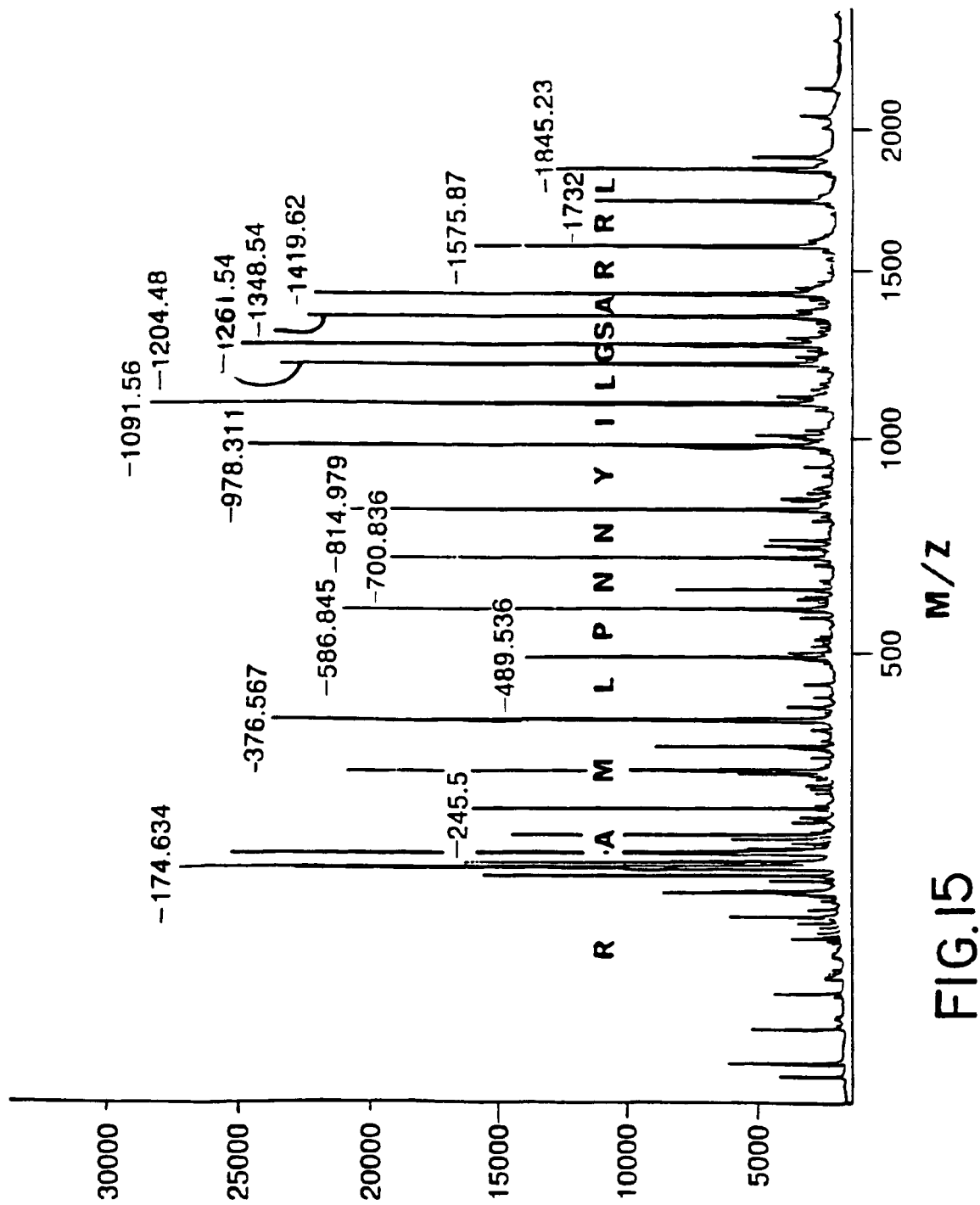
FIG. 15 shows the spectrum of the mixture (SEQ ID NO:7) obtained in Example 4.

Post-ninhydrin Experiment The machine-assisted assembly of the peptide LRRASGLIYNNPLMAR-amide (SEQ ID NO:24) was performed according to the in situ neutralization methods of Schnolzer and Kent (9) on a 0.25 mmol scale using MBHA resin and 2.2 mmol $N-\alpha$-Boc amino acids. The following side chain protecting groups were used: Arg, tosyl; Asn, xanthyl; Ser, benzyl(Bzl); Tyr, bromobenzyloxycarbonyl(BrZ). Resin samples were collected at each step in the synthesis and each sample was individually subjected to the quantitative ninhydrin reaction. These samples were then pooled and the Boc groups removed in neat TFA. Cleavage of the peptide fragments from the resin was performed by treatment with HF-10% p-cresol (° C., 1 hour). The resulting crude peptide products were precipitated and washed with ether, dissolved in 50% acetic acid, diluted with water and lyophillized. The mass spectrum of the mixture is shown in FIG. 15.

CITATIONS

The following publications are referred to in this specifications. The complete disclosure of each of them is hereby incorporated by references.

1. Aebersold et al, *Protein Science* 1, 494 (1992)
2. R. Self, A. Parente, *Biomed. Mass Spectrom.* 10, 78 (1983)
3. L. A. Smith, R. M. Caprioli, *Biomed. Mass Spectrom.* 10, 98 (1983)
4. B. T. Chait, T. Chaudhary, F. H. Field, "Methods in Protein sequence Analysis 1986", K. A. Walsh, ed., Humana Press 1987, pp. 483-493, and uncontrolled chemical degradation 5. A. Tsugita, K. Takamoto, M. Kamo, H. Iwadate, *Eur. J. Biochem.* 206, 691 (1992)
6. G. E. Tarr (1977), in *Methods Enzymology* 47, 355.
7. R. C. Beavis and B. T. Chait (1989), *Rapid Commun. Mass Spectrom.* 3, 233.
8. S. B. H. Kent, *Annual Rev. Biochem.* 57, 957-984 (1988)
9. Schnolzer et al, *Int. J. Peptide Protein Res.* 40, 1992, 180-193
10. W. A. Schroeder, *Meth. Enzymol.* 25, 298 (1972)

What is claimed is:

1. A method for identifying a covalent modification of an amino acid residue in a polypeptide comprising:

(1) reacting the polypeptide having a covalent modification with a molar excess of a pair of reagents comprising phyenylisothiocyanate (PITC) as a coupling reagent and phenylisocyanate (PIC) as a terminating reagent each of which forms a reaction product with a terminal amino acid residue of the polypeptide to be analyzed under a basic reaction condition; the reaction product generated between the terminating reagent and the terminal amino acid residue of the polypeptide being stable under all subsequent conditions;

(2) changing the reaction conditions to acidic conditions so that the PITC terminal amino acid separates from the remainder of the peptide, forming a reaction mixture comprising:
   i. unreacted coupling and terminating reagents,
   ii. a first reaction product which is the reaction product between the polypeptide and the PIC terminating reagent; and
   iii. a newly formed polypeptide from which the terminal amino acid residue has been removed;

(3) repeating steps (1) and (2) any selected number of cycles thereby to form a final mixture which comprises:
   i. reaction product between the polypeptide and the PITC terminating reagent, and ii. a peptide ladder which is a series of adjacent reaction products which is formed by reaction between the terminating reagent and the terminal amino acid residue of a fraction of the newly generated polypeptide of each cycle; and (4) identifying the covalent modification by determining the differences in molecular mass between adjacent members of the series of reaction products by mass spectroscopy, said difference being equal to the molecular mass of the amino acid residue cleaved from the polypeptide and from each subsequent formed polypeptide of the series, said differences coupled with the positions of said adjacent members in the mass spectrum being indicative of the identity and position of the covalent modification in the polypeptide.

2. The method of claim 1 wherein the covalent modification is phosphorylation.

3. The method of claim 1 wherein the covalent modification is acetylation.

4. The method of claim 1 wherein the covalent modification is glycosylation.

5. The method of claim 1 wherein the covalent modification is a disulfide bond.

6. The method of claim 1, wherein said mass spectrometry is ion trap mass spectrometry.

7. The method of claim 1, wherein said mass spectrometry is quadrupole mass spectrometry.

* * * * *

```
                        SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
        (A) LENGTH: 20 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /product= "OTHER"
            /note= "Xaa = alpha-amino-n-butyric acid"

(xi) SEQUENCE DESCRIPTION: SEQ ID NO: 1:

Xaa Gly His Lys Ala Ile Gly Thr Val Leu Val Gly Pro Thr Pro Val
1               5                   10                  15

Asn Ile Ile Gly
            20

(2) INFORMATION FOR SEQ ID NO: 2:

(i) SEQUENCE CHARACTERISTICS:
        (A) LENGTH: 18 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 2:

Gly Ile Gly Gly Phe Ile Lys Val Arg Gln Tyr Asp Gln Ile Pro Val
1               5                   10                  15

Glu Ile (2) INFORMATION FOR SEQ ID NO: 3:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 3:

Leu Glu Glu Met Asn Leu Pro Gly Lys Trp Lys Pro Lys Met Ile Gly
1               5                   10                  15

(2) INFORMATION FOR SEQ ID NO: 4:

(i) SEQUENCE CHARACTERISTICS:
        (A) LENGTH: 16 amino acids
        (B) TYPE: amino acid
```

```
        (C) STRANDEDNESS: <Unknown>
        (D) TOPOLOGY: linear (ii) MOLECULE TYPE: peptide (xi) SEQUENCE DESCRIPTION: SEQ ID NO: 4:

Leu Arg Arg Ala Phe Gly Leu Ile Gly Asn Asn Pro Leu Met Ala Arg
1               5                   10                  15

(2) INFORMATION FOR SEQ ID NO: 5:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = phosphorylated serine"

(xi) SEQUENCE DESCRIPTION: SEQ ID NO: 5:

Leu Arg Arg Ala Xaa Gly Leu Ile Tyr Asn Asn
1               5                   10

(2) INFORMATION FOR SEQ ID NO: 6:

(i) SEQUENCE CHARACTERISTICS:
        (A) LENGTH: 11 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 6:

Leu Arg Arg Ala Ser Gly Leu Ile Tyr Asn Asn
1               5                   10

(2) INFORMATION FOR SEQ ID NO: 7:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 7:

Leu Arg Arg Ala Ser Gly Leu Ile Tyr Asn Asn Pro Leu Met Ala Arg
1               5                   10                  15

(2) INFORMATION FOR SEQ ID NO: 8:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 8:

Gly Leu Val Phe Ala
1               5
```

(2) INFORMATION FOR SEQ ID NO: 9:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 9:

Leu Val Phe Ala
1

(2) INFORMATION FOR SEQ ID NO: 10:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 16
        (D) OTHER INFORMATION: /product= "OTHER"
            /note= "Xaa = argininamide"

(xi) SEQUENCE DESCRIPTION: SEQ ID NO: 10:

Leu Arg Arg Ala Ser Gly Leu Ile Tyr Asn Asn Thr Leu Met Ala Xaa
1               5                   10                  15

(2) INFORMATION FOR SEQ ID NO: 11:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 11:

Ala Val Gly Leu Phe Ala Gly
1               5

(2) INFORMATION FOR SEQ ID NO: 12:

(i) SEQUENCE CHARACTERISTICS:
        (A) LENGTH: 4 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 4
        (D) OTHER INFORMATION: /product= "OTHER"
            /note= "Xaa = glycine bound to a resin such as
            methylbenzhydrylamine"

(xi) SEQUENCE DESCRIPTION: SEQ ID NO: 12:

Leu Phe Ala Xaa
1

(2) INFORMATION FOR SEQ ID NO: 13:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 5
        (D) OTHER INFORMATION: /product= "OTHER"
            /note= "Xaa = glycine bound to a resin such as
            methylbenzhydrylamine"

(xi) SEQUENCE DESCRIPTION: SEQ ID NO: 13:

Gly Leu Phe Ala Xaa
1           5

(2) INFORMATION FOR SEQ ID NO: 14:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /product= "OTHER"
            /note= "Xaa = glycine bound to a resin such as
            methylbenzhydrylamine"

(xi) SEQUENCE DESCRIPTION: SEQ ID NO: 14:

Val Gly Leu Phe Ala Xaa
1           5

(2) INFORMATION FOR SEQ ID NO: 15:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 7
        (D) OTHER INFORMATION: /product= "OTHER"
            /note= "Xaa = glycine bound to a resin such as
            methylbenzhydrylamine"

(xi) SEQUENCE DESCRIPTION: SEQ ID NO: 15:

Ala Val Gly Leu Phe Ala Xaa
1           5

(2) INFORMATION FOR SEQ ID NO: 16:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 16:

Gly Phe Ala Leu Ile
1               5

(2) INFORMATION FOR SEQ ID NO: 17:

(i) SEQUENCE CHARACTERISTICS:
            (A) LENGTH: 4 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = 9-fluoromethoxycarbonyl (Fmoc)
                phenylalanine"

(ix) FEATURE:
            (A) NAME/KEY: Modified-site
            (B) LOCATION: 4
            (D) OTHER INFORMATION: /product= "OTHER"
                /note= "Xaa = isoleucine bound to a resin such as
                methylbenzhydrylamine"

(xi) SEQUENCE DESCRIPTION: SEQ ID NO: 17:

Xaa Ala Leu Xaa
1

(2) INFORMATION FOR SEQ ID NO: 18:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /product= "OTHER"
                /note= "Xaa = 9-fluoromethoxycarbonyl (Fmoc) glycine"

(ix) FEATURE:
            (A) NAME/KEY: Modified-site
            (B) LOCATION: 5
            (D) OTHER INFORMATION: /product= "OTHER"
                /note= "Xaa = isoleucine bound to a resin such as
                methylbenzhydrylamine"

(xi) SEQUENCE DESCRIPTION: SEQ ID NO: 18:

Xaa Phe Ala Leu Xaa
1               5

(2) INFORMATION FOR SEQ ID NO: 19:

(i) SEQUENCE CHARACTERISTICS:
            (A) LENGTH: 5 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 5
            (D) OTHER INFORMATION: /product= "OTHER"

```
            /note= "Xaa = isoleucine bound to a resin such as
             methylbenzhydrylamine"

(xi) SEQUENCE DESCRIPTION: SEQ ID NO: 19:

Gly Phe Ala Leu Xaa
1               5

(2) INFORMATION FOR SEQ ID NO: 20:

(i) SEQUENCE CHARACTERISTICS:
        (A) LENGTH: 14 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 20:

Glu Gly Val Asn Asp Asn Glu Glu Gly Phe Phe Ser Ala Arg
1               5                   10

(2) INFORMATION FOR SEQ ID NO: 21:

(i) SEQUENCE CHARACTERISTICS:
        (A) LENGTH: 99 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 67
        (D) OTHER INFORMATION: /product= "OTHER"
            /note= "Xaa = alpha-amino-n-butyric acid"

(ix) FEATURE:
        (A) NAME/KEY: Modified-site
        (B) LOCATION: 95
        (D) OTHER INFORMATION: /product= "OTHER"
            /note= "Xaa = alpha-amino-n-butyric acid"

(xi) SEQUENCE DESCRIPTION: SEQ ID NO: 21:

Pro Gln Ile Thr Leu Trp Gln Arg Pro Leu Val Thr Ile Arg Ile Gly
1               5                   10                  15

Gly Gln Leu Lys Glu Ala Leu Leu Asp Thr Gly Ala Asp Asp Thr Val
                20                  25                  30

Leu Glu Glu Met Asn Leu Pro Gly Lys Trp Lys Pro Lys Met Ile Gly
        35                  40                  45

Gly Ile Gly Gly Phe Ile Lys Val Arg Gln Tyr Asp Gln Ile Pro Val
    50                  55                  60

Glu Ile Xaa Gly His Lys Ala Ile Gly Thr Val Leu Val Gly Pro Thr
65                  70                  75                  80

Pro Val Asn Ile Ile Gly Arg Asn Leu Leu Thr Gln Ile Gly Xaa Thr
                85                  90                  95

Leu Asn Phe (2) INFORMATION FOR SEQ ID NO: 22:

(i) SEQUENCE CHARACTERISTICS:
        (A) LENGTH: 54 amino acids
        (B) TYPE: amino acid
        (C) STRANDEDNESS: <Unknown>
        (D) TOPOLOGY: linear (ii) MOLECULE TYPE: peptide
```

-continued (xi) SEQUENCE DESCRIPTION: SEQ ID NO: 22:

Leu Glu Glu Met Asn Leu Pro Gly Lys Trp Lys Pro Lys Met Ile Gly
1               5                   10                  15

Gly Ile Gly Gly Phe Ile Lys Val Arg Gln Tyr Asp Gln Ile Pro Val
                20                  25                  30

Glu Ile Xaa Gly His Lys Ala Ile Gly Thr Val Leu Val Gly Pro Thr
            35                  40                  45

Pro Val Asn Ile Ile Gly
    50

(2) INFORMATION FOR SEQ ID NO: 23:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 16
        (D) OTHER INFORMATION: /product= "OTHER"
            /note= "Xaa = argininamide"

(xi) SEQUENCE DESCRIPTION: SEQ ID NO: 23:

Leu Arg Arg Ala Phe Gly Leu Ile Gly Asn Asn Pro Leu Met Ala Xaa
1               5                   10                  15

(2) INFORMATION FOR SEQ ID NO: 24:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 16
        (D) OTHER INFORMATION: /product= "OTHER"
            /note= "Xaa = argininamide"

(xi) SEQUENCE DESCRIPTION: SEQ ID NO: 24:

Leu Arg Arg Ala Ser Gly Leu Ile Tyr Asn Asn Pro Leu Met Ala Xaa
1               5                   10                  15